United States Patent
Klaiman et al.

(10) Patent No.: US 10,916,009 B2
(45) Date of Patent: Feb. 9, 2021

(54) OBJECT IDENTIFICATION

(71) Applicant: SYNC-RX LTD., Netanya (IL)

(72) Inventors: Eldad Klaiman, Herzlia (IL); Alexander Steinbert, Ra'anana (IL); Nili Karmon, Tel Aviv (IL); Sarit Semo, Ra'anana (IL); Ran Cohen, Petah Tikva (IL)

(73) Assignee: SYNC-RX LTD., Netanya (IL)

( * ) Notice: Subject to any disclaimer, the term of this patent is extended or adjusted under 35 U.S.C. 154(b) by 201 days.

(21) Appl. No.: 16/213,696

(22) Filed: Dec. 7, 2018

(65) Prior Publication Data
US 2020/0085386 A1 Mar. 19, 2020

Related U.S. Application Data

(63) Continuation of application No. 15/311,171, filed as application No. PCT/IL2015/050509 on May 13, 2015, now Pat. No. 10,152,788.
(Continued)

(51) Int. Cl.
*A61B 6/12* (2006.01)
*G06T 7/00* (2017.01)
(Continued)

(52) U.S. Cl.
CPC .............. *G06T 7/0012* (2013.01); *A61B 6/12* (2013.01); *A61B 6/4441* (2013.01); *A61B 6/463* (2013.01);
(Continued)

(58) Field of Classification Search
CPC ......... A61B 6/12; A61B 6/4441; A61B 6/463; A61B 6/487; A61B 6/503; A61B 6/504;
(Continued)

(56) References Cited

U.S. PATENT DOCUMENTS

| 4,916,533 A * | 4/1990 | Gillies | A61B 1/00147 348/65 |
| 8,641,753 B2 | 2/2014 | MacAtangay | A61F 2/07 623/1.13 |

(Continued)

FOREIGN PATENT DOCUMENTS

| WO | 2008107905 A3 | 12/2008 |
| WO | 2009153794 A1 | 12/2009 |

(Continued)

OTHER PUBLICATIONS

Frenkel, Max et al "Curve Matching using the Fast Marching Method", Network and Parallel Computing, Jan. 2003, vol. 2683, pp. 35-51.

(Continued)

*Primary Examiner* — Mekonen T Bekele

(57) ABSTRACT

Apparatus and methods are described including, using a computer processor (28), automatically identifying whether a given pixel (111) within an image corresponds to a portion of an object. A set of concentric circles (132*a-c*) that are disposed around the pixel are sampled, and a first function is applied to each of the circles such that the circles are defined by a first set of rotationally invariant descriptors. A second function is applied to the set of circles to generate a second set of descriptors, each of which represents a difference between respective pairs of the circles. A third function is applied such that the second set of descriptors becomes rotationally invariant. The processor identifies whether the given pixel corresponds to the portion of the object, based upon the first and second sets of rotationally invariant descriptors. Other applications are also described.

11 Claims, 14 Drawing Sheets

Related U.S. Application Data

(60) Provisional application No. 61/993,123, filed on May 14, 2014.

(51) Int. Cl.
| | | |
|---|---|---|
| *G06T 7/73* | (2017.01) | |
| *G06T 7/33* | (2017.01) | |
| *A61B 6/00* | (2006.01) | |
| *G06N 20/00* | (2019.01) | |
| *G06T 7/30* | (2017.01) | |
| *G06T 7/70* | (2017.01) | |
| *A61B 8/08* | (2006.01) | |
| *A61B 8/12* | (2006.01) | |
| *G16H 30/20* | (2018.01) | |
| *A61M 25/09* | (2006.01) | |
| *A61M 25/01* | (2006.01) | |

(52) U.S. Cl.
CPC ............ *A61B 6/487* (2013.01); *A61B 6/503* (2013.01); *A61B 6/504* (2013.01); *A61B 6/5211* (2013.01); *A61B 6/5217* (2013.01); *A61B 6/5235* (2013.01); *A61B 8/0841* (2013.01); *A61B 8/12* (2013.01); *A61B 8/5215* (2013.01); *G06N 20/00* (2019.01); *G06T 7/30* (2017.01); *G06T 7/33* (2017.01); *G06T 7/337* (2017.01); *G06T 7/70* (2017.01); *G06T 7/73* (2017.01); *G06T 7/74* (2017.01); *A61M 25/09* (2013.01); *A61M 2025/0166* (2013.01); *G06T 2207/10081* (2013.01); *G06T 2207/10101* (2013.01); *G06T 2207/10108* (2013.01); *G06T 2207/10121* (2013.01); *G06T 2207/20081* (2013.01); *G06T 2207/30021* (2013.01); *G06T 2207/30101* (2013.01); *G16H 30/20* (2018.01)

(58) Field of Classification Search
CPC ... A61B 6/5211; A61B 6/5217; A61B 6/5235; A61B 8/0841; A61B 8/12; A61B 8/5215; G06N 20/00; G06T 7/0012; G06T 7/30; G06T 7/33; G06T 7/337; G06T 7/70; G06T 7/73; G06T 7/74; G06T 2207/10081; G06T 2207/10101; G06T 2207/10108; G06T 2207/10121; G06T 2207/20081; G06T 2207/30021; G06T 2207/30101; G16H 50/30; G16H 30/20; A61M 2025/0166; A61M 25/09
See application file for complete search history.

(56) References Cited

U.S. PATENT DOCUMENTS

| | | | | |
|---|---|---|---|---|
| 8,687,891 | B2* | 4/2014 | Takacs | G06K 9/527 |
| | | | | 382/190 |
| 8,926,687 | B2 | 1/2015 | Macatangay | A61F 2/07 |
| | | | | 623/1.13 |
| 2004/0215235 | A1 | 10/2004 | Jackson et al. | |
| 2005/0141766 | A1 | 6/2005 | Nagahashi | G06K 9/00248 |
| | | | | 382/190 |
| 2006/0015011 | A1* | 1/2006 | Hasegawa | G06T 7/73 |
| | | | | 600/117 |
| 2006/0155327 | A1 | 7/2006 | Briganti et al. | |
| 2006/0257006 | A1* | 11/2006 | Bredno | A61B 6/481 |
| | | | | 382/128 |
| 2008/0137923 | A1 | 6/2008 | Spahn | |
| 2008/0221440 | A1 | 9/2008 | Iddan et al. | |
| 2008/0275335 | A1* | 11/2008 | Zhang | A61B 6/12 |
| | | | | 600/424 |
| 2009/0163800 | A1* | 6/2009 | Xu | A61B 6/566 |
| | | | | 600/424 |
| 2009/0208071 | A1* | 8/2009 | Nishimura | G06T 7/0012 |
| | | | | 382/128 |
| 2009/0245601 | A1 | 10/2009 | Cohen et al. | |
| 2009/0306547 | A1 | 12/2009 | Iddan et al. | |
| 2010/0198333 | A1 | 8/2010 | Macatangay | A61F 2/07 |
| | | | | 623/1.15 |
| 2010/0222671 | A1 | 9/2010 | Coken et al. | |
| 2010/0318115 | A1 | 12/2010 | Chandusko et al. | |
| 2011/0286627 | A1 | 11/2011 | Takacs | G06K 9/4642 |
| | | | | 382/103 |
| 2012/0004537 | A1 | 1/2012 | Tolkowsky et al. | |
| 2012/0230565 | A1 | 9/2012 | Steinberg et al. | |
| 2012/0300981 | A1 | 11/2012 | Yeh et al. | |
| 2014/0039316 | A1* | 2/2014 | Ichioka | A61B 8/483 |
| | | | | 600/439 |
| 2014/0094691 | A1* | 4/2014 | Steinberg | A61B 5/061 |
| | | | | 600/424 |
| 2014/0111541 | A1 | 4/2014 | Tolkowsky | A61B 5/0044 |
| | | | | 345/632 |
| 2014/0121513 | A1 | 5/2014 | Tolkowsky et al. | |
| 2014/0140597 | A1 | 5/2014 | Barzelay et al. | |
| 2014/0163694 | A1 | 6/2014 | Macatangay | A61F 2/07 |
| | | | | 623/23.69 |
| 2014/0276684 | A1* | 9/2014 | Huennekens | A61B 17/320758 |
| | | | | 606/7 |
| 2015/0125052 | A1 | 5/2015 | Wong | G06K 9/46 |
| | | | | 382/128 |
| 2017/0076446 | A1 | 3/2017 | Pedersen | G06T 7/0012 |

FOREIGN PATENT DOCUMENTS

| | | |
|---|---|---|
| WO | 2011145094 A2 | 11/2011 |
| WO | 2012014212 A2 | 2/2012 |
| WO | 2013128233 A1 | 9/2013 |
| WO | 2013174472 A3 | 11/2013 |
| WO | 2014002095 A3 | 1/2014 |
| WO | 2015155770 A1 | 10/2015 |
| WO | 2010058398 A3 | 5/2016 |

OTHER PUBLICATIONS

Frenay, Benoit "Curve Alignment: Theory and Applications", Jun. 2012, Retrieved from the Internet URL:https://samm.univ-paris1.fr/IMG/pdf/frenay.pdf.

He, Mingyi et al "Rotation Invariant Feature Descriptor Integrating HAVA and RIFT", Proceedings of the Second APSIPA Annual Summit and Conference, Dec. 2010, pp. 935-938.

Zhang, Dengsheng et al "Shape-based Image Retrieval using Generic Fourier Descriptor", Signal Processing Image Communication, vol. 17, No. 10, Nov. 2002.

Stefanou, Stefanos et al "Efficient Scale and Rotation Invariant Object Detection based on HOGs and Evolutionary Optimization Techiques".

Maenpaa, Topi "The Local Binary Pattern Approach to Texture Analysis—Extensions and Applications", Academic Dissertation—University of Oulo, Aug. 2003.

E.W. Dijkstra, (1959) "A Note on Two Problems in Connexion with Graphs", Numerische Mathematik 1, pp. 269-271.

Alejandro F. Frangi, et al., (1998) "Multiscale vessel enhancement filtering" In Medical Image Computing and Computer Assisted Intervention—MICCAI'98, Lecture Notes in Computer Science, vol. 1496, Springer Verlag, Berlin, Germany, pp. 130-137.

* cited by examiner

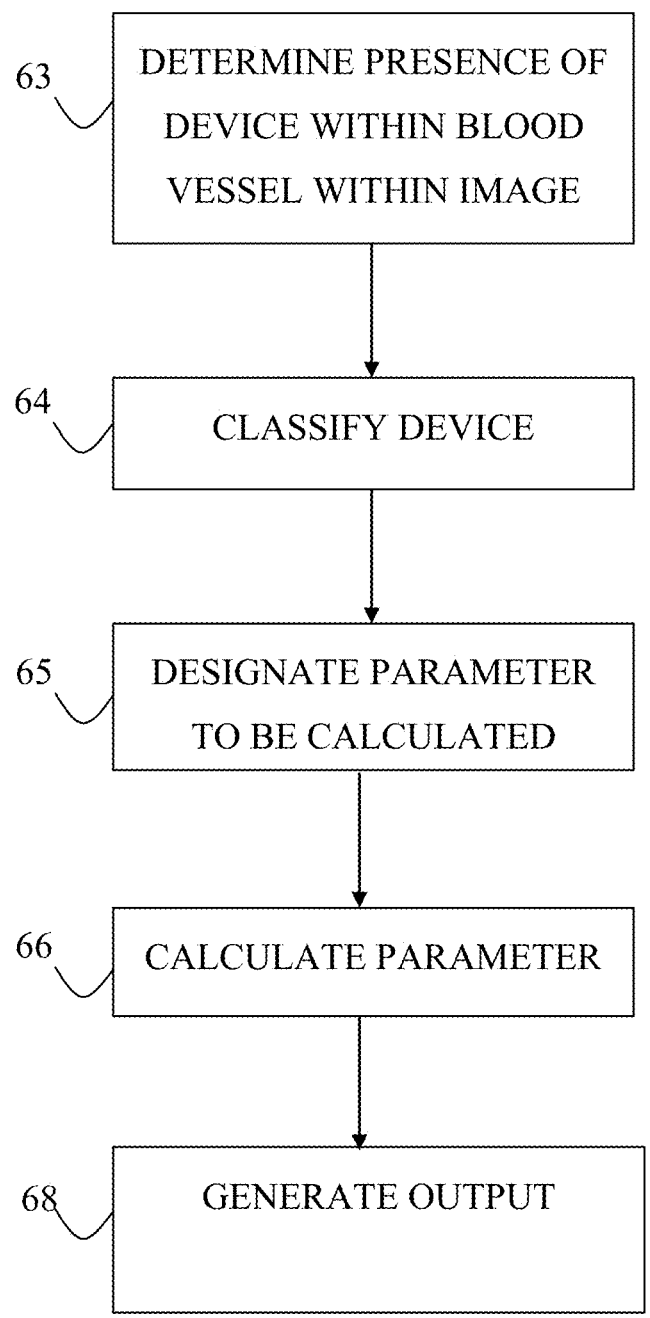

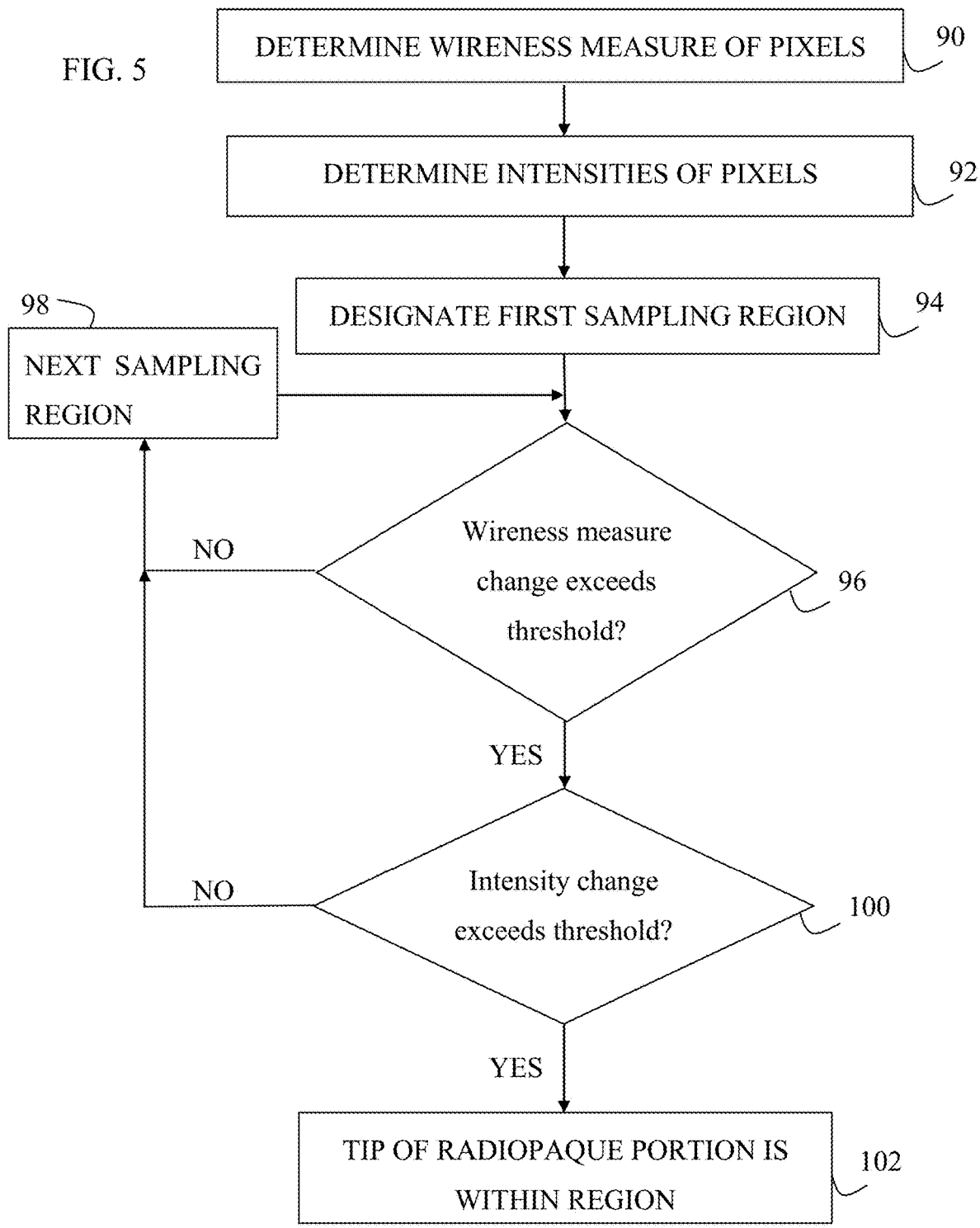

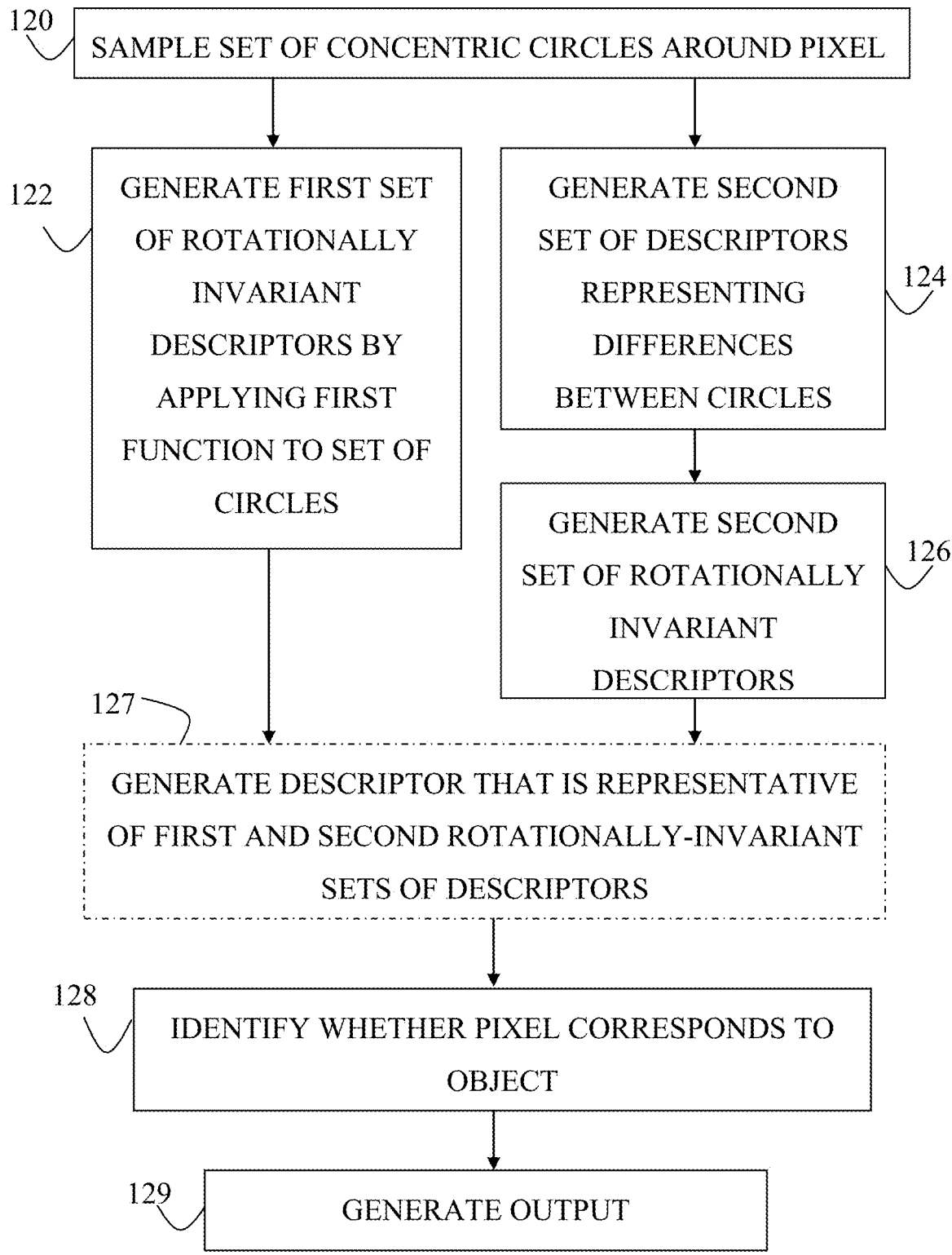

FIG. 9A
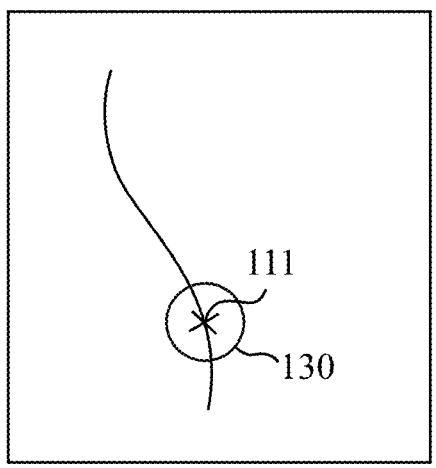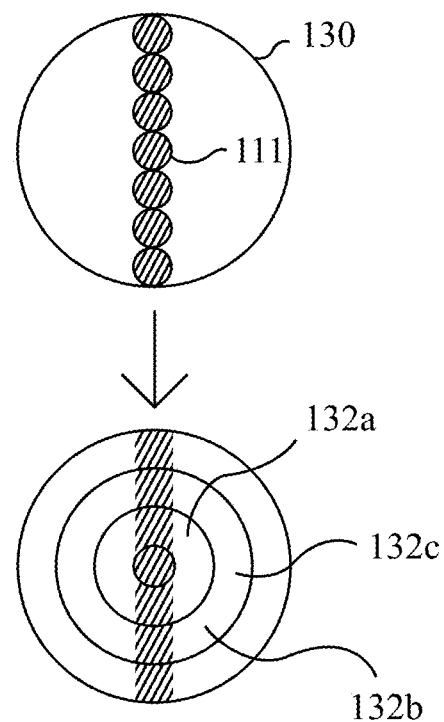
FIG. 9B
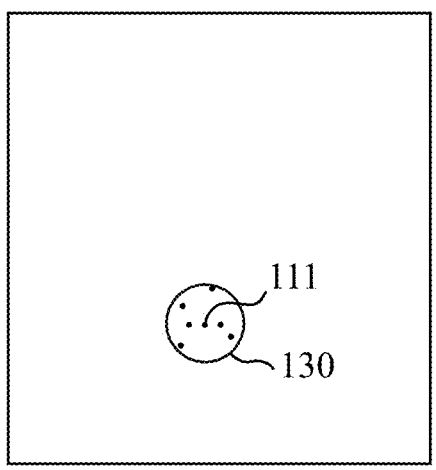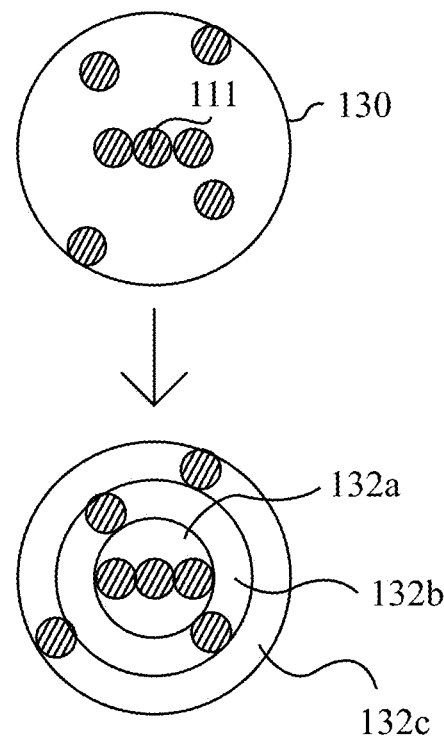

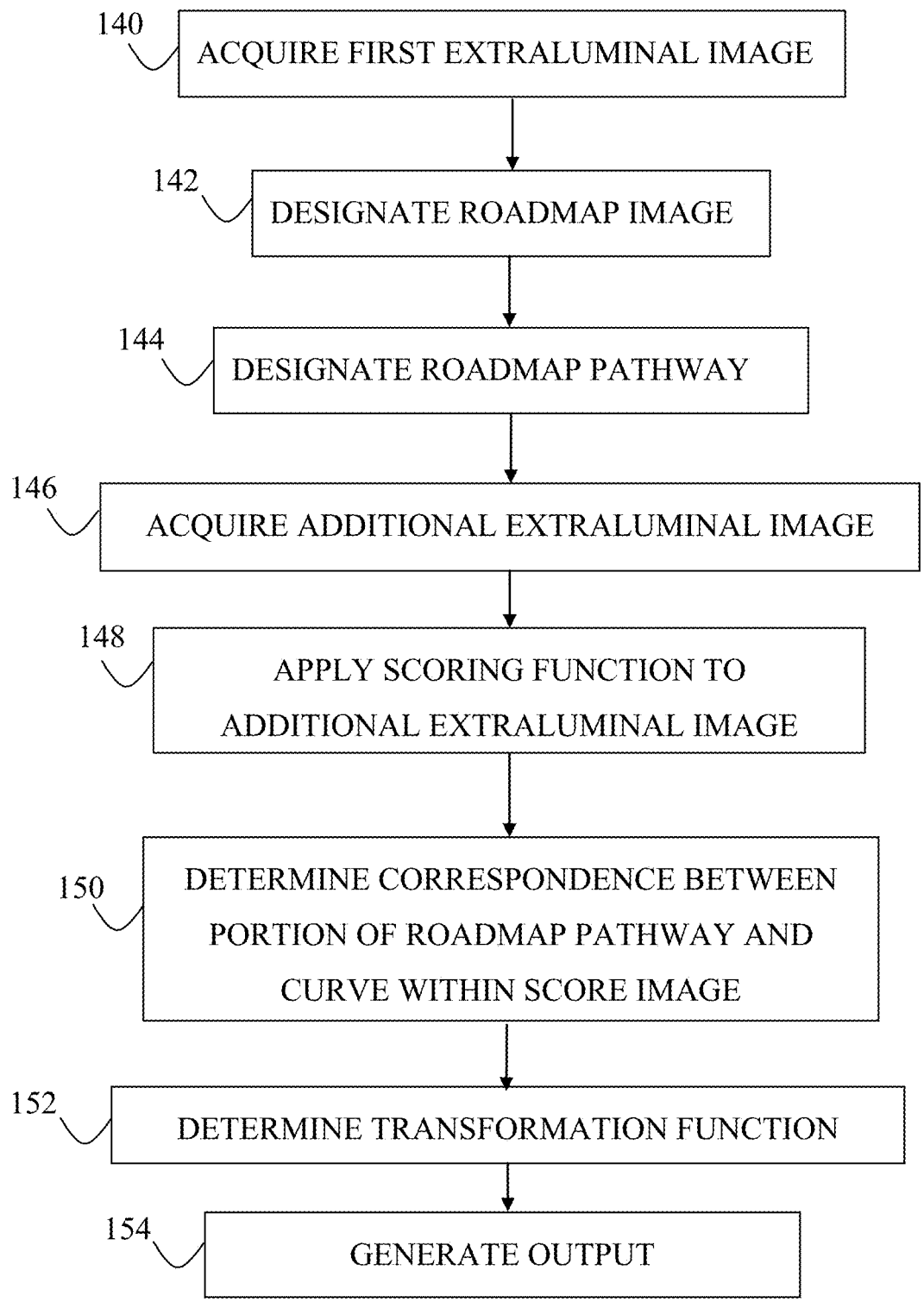

OBJECT IDENTIFICATION

CROSS REFERENCES TO RELATED APPLICATIONS

The present application is a continuation of U.S. patent application Ser. No. 15/311,171, filed Nov. 14, 2016, now U.S. patent Ser. No. 10/152,788, which is a US national stage entry of International Application No. PCT/IL2015/050509, filed May 13, 2015, which claims priority from U.S. Provisional Patent Application No. 61/993,123 to Klaiman, filed May 14, 2014, entitled "Image analysis in the presence of a medical device," each of which is incorporated herein by reference.

FIELD OF EMBODIMENTS OF THE INVENTION

Some applications of the present invention generally relate to medical imaging. Specifically, some applications of the present invention relate to medical imaging and analysis of such images when such images are acquired in the presence of a tool in the subject's body.

BACKGROUND

Vascular catheterizations, such as coronary catheterizations, are frequently-performed medical interventions. Such interventions are typically performed in order to diagnose the blood vessels for potential disease, and/or to treat diseased blood vessels. Typically, in order to enable observation of blood vessels, the catheterization is performed under extraluminal imaging. Additionally, for some procedures, an endoluminal data-acquisition device is used to perform endoluminal imaging and/or measurements. The extraluminal imaging and, where applicable, the endoluminal data are typically evaluated by the medical staff in combination with one another in the course of the intervention, as well as post procedurally.

SUMMARY OF EMBODIMENTS

For some applications of the present invention, a computer processor analyzes a given pixel of an image such as to automatically identify whether the pixel corresponds to a portion of an object within the image. Typically, the analysis is performed with respect to an image (e.g., a fluoroscopic image) of a blood vessel of a subject, and is used to identify whether the given pixel within the image corresponds to a portion of an object (e.g., a device) that is disposed inside the blood vessel. For example, the object disposed within the blood vessel may be a guide catheter, a wire (e.g., a guidewire), a therapeutic endoluminal device, an endoluminal data-acquisition device, a radiopaque marker, and/or a stent.

In order to analyze the pixel, the computer processor samples a set of concentric circles that are disposed around the pixel. The computer processor applies a first function to each of the circles such that the circles are defined by a first set of rotationally invariant descriptors. For example, the computer processor may apply a time-frequency domain transform (e.g., a Fourier transform, a discrete sine transform, and/or a discrete cosine transform) to the circles, and the computer processor may determine the absolute coefficients of the time-frequency domain transform of each of the circles.

The computer processor applies a second function to the set of circles such as to generate a second set of descriptors, each of the second set of descriptors representing a difference between respective pairs of the circles. The computer processor then applies a third function to the second set of descriptors, such that the second set of descriptors forms a second set of rotationally invariant descriptors, by becoming rotationally invariant. For example, the computer processor may apply a time-frequency domain transform (e.g., a Fourier transform, a discrete sine transform, and/or a discrete cosine transform) to the second set of descriptors, and the computer processor may determine the absolute coefficients of the time-frequency domain transform of each of the second set of descriptors.

For some applications, the computer processor generates a representative descriptor that is representative of a combination of the first and second sets of rotationally invariant descriptors.

For some applications, the computer processor first generates a set of descriptors representing differences between respective pairs of circles. Subsequently, the computer processor generates first and second rotationally invariant descriptors by (a) applying a time-frequency domain transform (e.g., a Fourier transform, a discrete sine transform, and/or a discrete cosine transform) to both the circles and to the set of descriptors representing the differences between respective pairs of circles, and (b) determining the absolute coefficients of the resultant time-frequency domain transforms. Typically, the output of these steps is a descriptor that is representative of sets of rotationally invariant descriptors of both the circles and the differences between the circles.

The representative descriptor is rotationally invariant with respect to the region that is sampled around the pixel, and such that the rotational alignment of the concentric circles with respect to each other is defined. The computer processor identifies whether the given pixel corresponds to the portion of the object, based upon the representative descriptor and/or based upon the first and second sets of rotationally invariant descriptors, e.g., by applying machine-learning classifying to the representative descriptor and/or to the first and second sets of rotationally invariant descriptors. The computer processor generates an output at least partially in response to identifying that the given pixel corresponds to the portion of the object.

For some applications, the location of the object within the image is determined by performing the above-described analysis with respect to a plurality of pixels within the image. For some applications, in response to determining the location of the object within a given image, the image is aligned with a second image, by aligning the locations of the object in each of the images with one another. Alternatively or additionally, identification of the location of the object within a given image is used to facilitate the determination of the location of an endoluminal device within the lumen, for example, in accordance with techniques described in US 2012/0004537 to Tolkowsky, US 2014/0094691 to Steinberg, and/or WO 13/175472 to Steinberg, which are incorporated herein by reference. Further alternatively or additionally, identification of the location of the object within a given image is used to facilitate the determination of a transformation function for mapping between the image and a second image, for example, in accordance with techniques described in US 2014/0094691 to Steinberg, and/or in WO 13/175472 to Steinberg, both of which applications are incorporated herein by reference.

For some applications of the present invention, a computer processor determines a transformation function for mapping between a location within an extraluminal roadmap image of a lumen and a location within a second extraluminal image of the lumen. Typically, at least one first extraluminal image of the lumen is acquired, and the computer processor designates the at least one first extraluminal image as a roadmap image. Further typically, a first set of extraluminal images of the lumen is acquired, and the computer processor designates at least one of the first set of images as a roadmap image. The computer processor designates a roadmap pathway within the roadmap image.

At least one additional extraluminal image is acquired. Typically, a second set of extraluminal images of the lumen is acquired. Further typically, the second set of extraluminal images are fluoroscopic images, at least some of which are acquired in an absence of contrast agent within the lumen, and, further typically, while an endoluminal device (e.g., an endoluminal data-acquisition device, or an endoluminal therapeutic device) is disposed within the lumen.

The computer processor generates a score image, by applying a scoring function to at least some pixels within the additional extraluminal image (e.g., an image belonging to a second set of extraluminal images), such that each of the pixels to which the scoring function is applied is designated a score that is indicative of an extent to which the pixel has a given characteristic. It is noted that, for some applications, the scoring function does not result in identifying a pixel as corresponding to a given object (such as a guide catheter, a wire, or a radiopaque marker). For some applications, a single filter is applied to the image. For example, a Hessian filter or a high pass filter may be applied to at least a portion of the image. For some applications, the scoring function designates a score to each of the pixels that is indicative of an intensity of the pixel. Alternatively or additionally, the scoring function designates a score to each of the pixels that is indicative of an extent to which the pixel is likely to correspond to a non-anatomical object.

Based upon the scores of at least some of the pixels to which the scoring function was applied, the computer processor determines a correspondence between a portion of the roadmap pathway and a curve within the score image. Typically, the computer processor determines the correspondence between the portion of the roadmap pathway and a curve within the score image, by applying a best-fit algorithm, such as to best fit the roadmap pathway to pixels of the image, the scores of which pixels indicate that the pixels are likely to correspond to pixels of the roadmap pathway.

Based upon the correspondence between the portion of the roadmap pathway and the curve within the score image, the computer processor determines the transformation function for mapping between the location within the roadmap image and the location within the additional extraluminal image (e.g., an image belonging to a second set of extraluminal images). In response to the determined transformation function, the computer processor generates an output.

For some applications, based upon the determined transformation function, the computer processor determines the location of an endoluminal device within the lumen, for example, in accordance with techniques described in US 2014/0094691 to Steinberg, and/or WO 13/175472 to Steinberg, both of which applications are incorporated herein by reference. For example, the additional extraluminal image may be acquired while the endoluminal device is inside the lumen. Based upon the transformation function, the computer processor may determine the location of the endoluminal device with respect to the roadmap image, and may generate an output indicative of the determined location of the endoluminal device with respect to the roadmap image.

For some applications, based upon the transformation function, the computer processor determines the location within the lumen at which one or more endoluminal data points were acquired by an endoluminal data-acquisition device (e.g., an endoluminal imaging device, or an endoluminal data-acquisition device that is configured to acquire a plurality of functional endoluminal data points). Based upon the determined locations within the lumen at which the endoluminal data points were acquired, the computer processor may generate an output, such as by generating an endoluminal imaging stack, and/or by generating an indication of the correspondence between an endoluminal data point and the location within the lumen at which the endoluminal data point was acquired. Alternatively, based upon the determined locations within the lumen at which the endoluminal data point was acquired, the computer processor may co-use endoluminal data points and extraluminal imaging using techniques described hereinabove, and/or as described in US 2012/0004537 to Tolkowsky, US 2014/0094691 to Steinberg, and/or WO 13/175472 to Steinberg, which are incorporated herein by reference.

There is therefore provided, in accordance with some applications of the present invention, a method for use with an image that contains an object, including:

using at least one computer processor, automatically identifying whether a given pixel within the image corresponds to a portion of the object, by:

sampling, from the image, a set of concentric circles that are disposed around the pixel;

applying a first function to each of the circles such that the circles are defined by a first set of rotationally invariant descriptors;

applying a second function to the set of circles such as to generate a second set of descriptors, each of the second set of descriptors representing a difference between respective pairs of the circles;

applying a third function to the second set of descriptors, such that the second set of descriptors forms a second set of rotationally invariant descriptors, by becoming rotationally invariant; and identifying whether the given pixel corresponds to the portion of the object, based upon the first and second sets of rotationally invariant descriptors; and generating an output at least partially in response to identifying that the given pixel corresponds to the portion of the object.

For some applications, identifying whether the given pixel corresponds to the portion of the object, based upon the first and second sets of rotationally invariant descriptors includes applying machine learning classifying to the first and second sets of rotationally invariant descriptors.

For some applications, the method further includes selecting the pixel to which the identifying is applied by:

for each pixel within at least a portion of the image, determining an objectness measure that measures an extent to which the pixel, together with other pixels within the image, forms part of a set of pixels having a given characteristic that is associated with the portion of the object; and selecting the pixel to which the identifying is applied by selecting a pixel selected form the group consisting of: a pixel disposed in a vicinity of at least some pixels that form part of the set of pixels, and a pixel that belongs to the set of pixels.

the method is for use with an image of a blood vessel of a subject, and automatically identifying whether the given pixel within the image corresponds to the portion of the object includes automatically identifying whether the given pixel within the image corresponds to a portion of an object that is disposed inside the blood vessel.

For some applications, automatically identifying whether the given pixel within the image corresponds to the portion of the object includes automatically identifying whether the given pixel within the image corresponds to a portion of an object disposed inside the blood vessel selected from the group consisting of: a guide catheter, a wire, an endoluminal imaging device, a radiopaque marker, and a stent.

For some applications, applying the first function to each of the circles such that the circles are defined by a first set of rotationally invariant descriptors includes calculating absolute coefficients of a time-frequency domain transform of each of the circles.

For some applications, calculating absolute coefficients of the time-frequency domain transform of each of the circles includes calculating absolute coefficients of a time-frequency domain transform of each of the circles, the time frequency domain transform being selected from the group consisting of: a Fourier transform, a discrete sine transform, and a discrete cosine transform.

For some applications, applying the third function to the second set of descriptors includes calculating absolute coefficients of a time-frequency domain transform of each of the second set of descriptors.

For some applications, calculating absolute coefficients of the time-frequency domain transform of each of the second set of descriptors includes calculating absolute coefficients of a time-frequency domain transform of each of the second set of descriptors, the time frequency domain transform being selected from the group consisting of: a Fourier transform, a discrete sine transform, and a discrete cosine transform.

For some applications, the method further includes aligning the image with a second image, at least partially in response to identifying that the given pixel corresponds to the portion of the object.

For some applications, generating the output includes, displaying the image and the second image in an image stream in which the image and the second image are aligned with one another.

For some applications, generating the output includes generating a composite image, based upon the alignment of the image and the second image.

For some applications, the method further includes determining a transformation function for mapping between the image and a second image, at least partially in response to identifying that the given pixel corresponds to the portion of the object, and generating the output includes generating the output based upon the determined transformation function.

For some applications:
the method is for use with an image of an endoluminal device disposed inside a blood vessel of a subject,
automatically identifying whether the given pixel within the image corresponds to the portion of the object includes automatically identifying whether the given pixel within the image corresponds to a portion of an object that is disposed inside the blood vessel,
the method further includes, based upon the determined transformation function, determining a location of the endoluminal device within the blood vessel, and
generating the output includes generating the output in response to the determined location of the endoluminal device.

For some applications:
the endoluminal device includes an endoluminal data-acquisition device,
determining the location of the endoluminal device within the blood vessel includes determining a location within the blood vessel at which an endoluminal data point was acquired by the endoluminal data-acquisition device, and
generating the output includes generating the output based upon determining the location within the blood vessel at which the endoluminal data point was acquired by the endoluminal data-acquisition device.

For some applications:
the method is for use with an image of an endoluminal device disposed inside a blood vessel of a subject,
automatically identifying whether the given pixel within the image corresponds to the portion of the object includes automatically identifying whether the given pixel within the image corresponds to a portion of an object that is disposed inside the blood vessel,
the method further includes, at least partially in response to identifying that the given pixel corresponds to the portion of the object, determining a location of the endoluminal device within the blood vessel, and
generating the output includes generating the output in response to the determined location of the endoluminal device.

For some applications:
the endoluminal device includes an endoluminal data-acquisition device,
determining the location of the endoluminal device within the blood vessel includes determining a location within the blood vessel at which an endoluminal data point was acquired by the endoluminal data-acquisition device, and
generating the output includes generating the output based upon determining the location within the blood vessel at which the endoluminal data point was acquired by the endoluminal data-acquisition device.

There is additionally provided, in accordance with some applications of the present invention, apparatus for use with an image that contains an object, including:
an output device; and
at least one computer processor configured to:
automatically identify whether a given pixel within the image corresponds to a portion of the object, by:
sampling, from the image, a set of concentric circles that are disposed around the pixel;
applying a first function to each of the circles such that the circles are defined by a first set of rotationally invariant descriptors;
applying a second function to the set of circles such as to generate a second set of descriptors, each of the second set of descriptors representing a difference between respective pairs of the circles;
applying a third function to the second set of descriptors, such that the second set of descriptors forms a second set of rotationally invariant descriptors, by becoming rotationally invariant; and
identifying whether the given pixel corresponds to the portion of the object, based upon the first and second sets of rotationally invariant descriptors; and
generate an output on the output device, at least partially in response to identifying that the given pixel corresponds to the portion of the object.

For some applications, the computer processor is configured to identify whether the given pixel corresponds to the portion of the object, by applying machine-learning classifying to the first and second sets of rotationally invariant descriptors.

For some applications, the computer processor is configured to select the pixel to which the identifying is applied by:

for each pixel within at least a portion of the image, determining an objectness measure that measures an extent to which the pixel, together with other pixels within the image, forms part of a set of pixels having a given characteristic that is associated with the portion of the object; and selecting the pixel to which the identifying is applied by selecting a pixel selected form the group consisting of: a pixel disposed in a vicinity of at least some pixels that form part of the set of pixels, and a pixel that belongs to the set of pixels.

For some applications, the apparatus is for use with an image of a blood vessel of a subject, and the computer processor is configured to automatically identify whether the given pixel within the image corresponds to the portion of the object by automatically identifying whether the given pixel within the image corresponds to a portion of an object that is disposed inside the blood vessel.

For some applications, the computer processor is configured to automatically identify whether the given pixel within the image corresponds to the portion of the object, by automatically identifying whether the given pixel within the image corresponds to a portion of an object disposed inside the blood vessel selected from the group consisting of: a guide catheter, a wire, an endoluminal imaging device, a radiopaque marker, and a stent.

For some applications, the computer processor is configured to apply the first function to each of the circles by calculating absolute coefficients of a time-frequency domain transform of each of the circles.

For some applications, the computer processor is configured to calculate absolute coefficients of the time-frequency domain transform of each of the circles by calculating absolute coefficients of a time-frequency domain transform of each of the circles, the time frequency domain transform being selected from the group consisting of: a Fourier transform, a discrete sine transform, and a discrete cosine transform.

For some applications, the computer processor is configured to apply the third function to the second set of descriptors by calculating absolute coefficients of a time-frequency domain transform of each of the second set of descriptors.

For some applications, the computer processor is configured to calculate absolute coefficients of the time-frequency domain transform of each of the second set of descriptors by calculating absolute coefficients of a time-frequency domain transform of each of the second set of descriptors, the time frequency domain transform being selected from the group consisting of: a Fourier transform, a discrete sine transform, and a discrete cosine transform.

For some applications, the computer processor is configured to align the image with a second image, at least partially in response to identifying that the given pixel corresponds to the portion of the object.

For some applications, the computer processor is configured to generate the output by displaying the image and the second image in an image stream in which the image and the second image are aligned with one another.

For some applications, the computer processor is configured to generate the output by generating a composite image, based upon the alignment of the image and the second image.

For some applications, the computer processor is configured to determine a transformation function for mapping between the image and a second image, at least partially in response to identifying that the given pixel corresponds to the portion of the object, and the computer processor is configured to generate the output based upon the determined transformation function.

For some applications:

the apparatus is for use with an image of an endoluminal device disposed within a blood vessel of a subject, the computer processor is configured to automatically identify whether the given pixel within the image corresponds to the portion of the object by automatically identifying whether the given pixel within the image corresponds to a portion of an object that is disposed inside the blood vessel, the computer processor is configured to determine a location of the endoluminal device within the blood vessel, based upon the determined transformation function, and the computer processor is configured to generate the output by generating the output in response to the determined location of the endoluminal device.

For some applications:

the endoluminal device includes an endoluminal data-acquisition device, the computer processor is configured to determine a location within the blood vessel at which an endoluminal data point was acquired by the endoluminal data-acquisition device, by determining the location of the endoluminal device within the blood vessel, and the computer processor is configured to generate the output by generating the output based upon determining the location within the blood vessel at which the endoluminal data point was acquired by the endoluminal data-acquisition device.

For some applications:

the apparatus is for use with an image of an endoluminal device disposed inside a blood vessel of a subject, the computer processor is configured to automatically identify whether the given pixel within the image corresponds to the portion of the object by automatically identifying whether the given pixel within the image corresponds to a portion of an object that is disposed inside the blood vessel, the computer processor is configured, at least partially in response to identifying that the given pixel corresponds to the portion of the object, to determine a location of the endoluminal device within the blood vessel, and the computer processor is configured to generate the output by generating the output in response to the determined location of the endoluminal device.

For some applications:

the endoluminal device includes an endoluminal data-acquisition device, the computer processor is configured to determine a location within the blood vessel at which an endoluminal data point was acquired by the endoluminal data-acquisition device, by determining the location of the endoluminal device within the blood vessel, and the computer processor is configured to generate the output by generating the output based upon determining the location within the blood vessel at which the endoluminal data point was acquired by the endoluminal data-acquisition device.

There is additionally provided, in accordance with some applications of the present invention, a computer software product, for use with an image that contains an object, the computer software product including a non-transitory computer-readable medium in which program instructions are stored, which instructions, when read by a computer cause the computer to perform the steps of automatically identifying whether a given pixel within the image corresponds to a portion of the object, by: sampling, from the image, a set of concentric circles that are disposed around the pixel; applying a first function to each of the circles such that the circles are defined by a first set of rotationally invariant descriptors; applying a second function to the set of circles such as to generate a second set of descriptors, each of the second set of descriptors representing a difference between respective pairs of the circles; applying a third function to the second set of descriptors, such that the second set of descriptors forms a second set of rotationally invariant descriptors, by becoming rotationally invariant; and identifying whether the given pixel corresponds to the portion of the object, based upon the first and second sets of rotationally invariant descriptors; and generating an output at least partially in response to identifying that the given pixel corresponds to the portion of the object.

There is further provided, in accordance with some applications of the present invention, a method for use with an extraluminal imaging device configured to acquire extraluminal images of a lumen of a body of a subject, and an output device, the method including:

using the extraluminal imaging device, acquiring at least one first extraluminal image of the lumen;

designating the at least one first extraluminal image as a roadmap image;

designating, within the roadmap image, a roadmap pathway;

acquiring at least one additional extraluminal image of the lumen;

generating a score image, by applying a scoring function to at least some pixels within the additional extraluminal image, such that each of the pixels to which the scoring function is applied is designated a score that is indicative of an extent to which the pixel has a given characteristic;

based upon the scores of at least some of the pixels to which the scoring function was applied, determining a correspondence between at least a portion of the roadmap pathway and a curve within the score image; and based upon the correspondence between the portion of the roadmap pathway and the curve within the score image, determining a transformation function for mapping between a location within the roadmap image and a location within the additional extraluminal image; and in response thereto, generating an output on the output device.

For some applications:

acquiring the at least one first extraluminal image of the lumen includes acquiring a first set of extraluminal images of the lumen; and designating the at least one first extraluminal image as the roadmap image includes designating at least one of the first set of extraluminal images as the roadmap image.

For some applications, applying the scoring function to at least some pixels within the additional extraluminal image includes applying a scoring function to at least some pixels within the additional extraluminal image such that each of the pixels to which the scoring function is applied is designated a score without identifying the pixel as corresponding to a given object.

For some applications, applying the scoring function to at least some pixels within the additional extraluminal image includes applying a single filter to the image.

For some applications, applying the scoring function to at least some pixels within the additional extraluminal image, includes applying a scoring function to at least some pixels within the image such that each of the pixels to which the scoring function is applied is designated a score that is indicative of an intensity of the pixel.

For some applications, applying the scoring function to at least some pixels within the additional extraluminal image, includes applying a scoring function to at least some pixels within the image such that each of the pixels to which the scoring function is applied is designated a score that is indicative of an extent to which the pixel is likely to correspond to a non-anatomical object.

For some applications, applying the scoring function to at least some pixels within the additional extraluminal image includes applying a high pass filter to at least a portion of the image.

For some applications, applying the scoring function to at least some pixels within the additional extraluminal image includes applying a Hessian filter to at least a portion of the image.

For some applications, acquiring the additional extraluminal image of the lumen includes acquiring the additional extraluminal image in an absence of contrast agent within the lumen.

For some applications, acquiring the additional extraluminal image of the lumen includes acquiring the additional extraluminal image while the lumen is at least partially visible due to a presence of contrast agent within the lumen.

For some applications, the method further includes, based upon the mapping, determining a plurality of local calibration factors associated with respective portions of the roadmap image.

For some applications, acquiring the at least one first extraluminal image of the lumen includes acquiring the at least one first extraluminal image of the lumen in an absence of contrast agent within the lumen.

For some applications, designating the roadmap pathway includes identifying a set of features within the roadmap image, and designating the roadmap pathway in response to the identified set of features.

For some applications, acquiring the at least one first extraluminal image of the lumen includes acquiring the at least one first extraluminal image of the lumen while the lumen is at least partially visible due to a presence of contrast agent within the lumen.

For some applications, designating the roadmap pathway includes identifying the lumen within the roadmap image, and designating a roadmap pathway that is disposed within the lumen.

For some applications, determining the correspondence between the portion of the roadmap pathway and the curve within the score image includes using a dynamic-programming algorithm to determine the correspondence between the portion of the roadmap pathway and the curve within the score image.

For some applications, determining the correspondence between the portion of the roadmap pathway and the curve within the score image includes:

determining a correspondence between a first pixel along the roadmap pathway and a first pixel of the additional extraluminal image; and determining a correspondence between a second pixel along the roadmap pathway and a second pixel of the additional extraluminal image, based upon:

the determined correspondence between the first pixel along the roadmap pathway and the first pixel of the additional extraluminal image, and the scores of at least some of the pixels to which the scoring function was applied.

For some applications, determining the correspondence between the portion of the roadmap pathway and the curve within the score image includes using a gradient-descent algorithm to determine the correspondence between the portion of the roadmap pathway and the curve within the score image.

For some applications, determining the correspondence between the portion of the roadmap pathway and the curve within the score image includes determining that pixels that are disposed in a given sequence in the additional extraluminal image correspond to respective pixels along the roadmap pathway, the corresponding pixels being disposed along the roadmap pathway in the same given sequence.

For some applications:

acquiring the at least one additional extraluminal image of the lumen includes acquiring a second set of extraluminal images while an endoluminal device is disposed inside the lumen, determining the transformation function for mapping between the location within the roadmap image and the location within the additional extraluminal image includes determining respective transformation functions for mapping between locations within the roadmap image and locations within respective image belonging to the second set of extraluminal images, and the method further includes, based upon the mapping, determining locations of the endoluminal device in respective extraluminal images of the second set of extraluminal images with respect to the roadmap image.

For some applications, determining locations of the endoluminal device in respective extraluminal images of the second set of extraluminal images with respect to the roadmap image includes, in real-time with respect to acquisitions of the extraluminal images of the second set of extraluminal images, determining locations of the endoluminal device in respective extraluminal images of the second set of extraluminal images with respect to the roadmap image, and generating the output includes generating an output that is indicative of the determined real-time location of the endoluminal device with respect to the roadmap image.

For some applications:

the endoluminal device includes a first endoluminal data-acquisition device configured to acquire a plurality of endoluminal data points while the endoluminal data-acquisition device is being moved through the lumen, the method further includes, based upon determining locations of the endoluminal device in respective extraluminal images of the second set of extraluminal images with respect to the roadmap image, co-registering respective endoluminal data points to respective locations within the roadmap image, and generating the output includes generating an output based upon the co-registration of the endoluminal data points to the respective locations within the roadmap image.

For some applications, the endoluminal data-acquisition device includes an endoluminal imaging device that is configured to acquire a plurality of endoluminal images while the endoluminal imaging device is being moved through the lumen, and co-registering respective endoluminal data points to respective locations within the roadmap image includes co-registering respective endoluminal images to respective locations within the roadmap image.

For some applications, the endoluminal data-acquisition device includes an endoluminal data-acquisition device that is configured to acquire functional data regarding the lumen, while the endoluminal data-acquisition device is being moved through the lumen, and co-registering respective endoluminal data points to respective locations within the roadmap image includes co-registering respective functional endoluminal data points to respective locations within the roadmap image.

For some applications, generating the output based upon the co-registration includes generating a stack of endoluminal data points, in which relative dispositions of endoluminal data points within the stack correspond to relative locations of the endoluminal data points with respect to the roadmap image.

There is further provided, in accordance with some applications of the present invention, apparatus for use with an extraluminal imaging device configured to acquire extraluminal images of a lumen of a body of a subject, the apparatus including:

an output device; and at least one computer processor configured to:

acquire at least one first extraluminal image of the lumen, using the extraluminal imaging device;

designate the at least one first extraluminal image as a roadmap image;

designate, within the roadmap image, a roadmap pathway;

acquire at least one additional extraluminal image of the lumen;

generate a score image, by applying a scoring function to at least some pixels within the additional extraluminal image, such that each of the pixels to which the scoring function is applied is designated a score that is indicative of an extent to which the pixel has a given characteristic;

based upon the scores of at least some of the pixels to which the scoring function was applied, determine a correspondence between at least a portion of the roadmap pathway and a curve within the score image;

based upon the correspondence between the portion of the roadmap pathway and the curve within the score image, determine a transformation function for mapping between a location within the roadmap image and a location within the additional extraluminal image; and in response thereto, generate an output on the output device.

For some applications, the computer processor is configured to:

acquire the at least one first extraluminal image of the lumen by acquiring a first set of extraluminal images of the lumen; and designate the at least one first extraluminal image as the roadmap image by designating at least one of the first set of extraluminal images as the roadmap image.

For some applications, the computer processor is configured to apply the scoring function to at least some pixels within the additional extraluminal image by applying a scoring function to at least some pixels within the additional extraluminal image such that each of the pixels to which the scoring function is applied is designated a score without identifying the pixel as corresponding to a given object.

For some applications, the computer processor is configured to apply the scoring function to at least some pixels within the additional extraluminal image, by applying a single filter to the image.

For some applications, the computer processor is configured to apply the scoring function to at least some pixels within the additional extraluminal image, by applying a scoring function to at least some pixels within the image such that each of the pixels to which the scoring function is applied is designated a score that is indicative of an intensity of the pixel.

For some applications, the computer processor is configured to apply the scoring function to at least some pixels within the additional extraluminal image, by applying a scoring function to at least some pixels within the image such that each of the pixels to which the scoring function is applied is designated a score that is indicative of an extent to which the pixel is likely to correspond to a non-anatomical object.

For some applications, the computer processor is configured to apply the scoring function to at least some pixels within the additional extraluminal image, by applying a high pass filter to at least a portion of the image.

For some applications, the computer processor is configured to apply the scoring function to at least some pixels within the additional extraluminal image, by applying a Hessian filter to at least a portion of the image.

For some applications, the computer processor is configured to acquire the additional extraluminal image of the lumen by acquiring the additional extraluminal image in an absence of contrast agent within the lumen.

For some applications, the computer processor is configured to acquire the additional extraluminal image of the lumen by acquiring the additional extraluminal image while the lumen is at least partially visible due to a presence of contrast agent within the lumen.

For some applications, the computer processor is configured to determine a plurality of local calibration factors associated with respective portions of the roadmap image, based upon the mapping.

For some applications, the computer processor is configured to acquire the at least one first extraluminal image of the lumen by acquiring the at least one first extraluminal image of the lumen in an absence of contrast agent within the lumen.

For some applications, the computer processor is configured to designate the roadmap pathway by identifying a set of features within the roadmap image, and designating the roadmap pathway in response to the identified set of features.

For some applications, the computer processor is configured to acquire the at least one first extraluminal image of the lumen by acquiring the at least one first extraluminal image of the lumen while the lumen is at least partially visible due to a presence of contrast agent within the lumen.

For some applications, the computer processor is configured to designate the roadmap pathway by identifying the lumen within the roadmap image, and designating a roadmap pathway that is disposed within the lumen.

For some applications, the computer processor is configured to determine the correspondence between the portion of the roadmap pathway and the curve within the score image, using a dynamic-programming algorithm.

For some applications, the computer processor is configured to determine the correspondence between the portion of the roadmap pathway and the curve within the score image by:
 determining a correspondence between a first pixel along the roadmap pathway and a first pixel of the additional extraluminal image; and
 determining a correspondence between a second pixel along the roadmap pathway and a second pixel of the additional extraluminal image, based upon:
  the determined correspondence between the first pixel along the roadmap pathway and the first pixel of the additional extraluminal image, and
  the scores of at least some of the pixels to which the scoring function was applied.

For some applications, the computer processor is configured to determine the correspondence between the portion of the roadmap pathway and the curve within the score image, using a gradient-descent algorithm.

For some applications, the computer processor is configured to determine the correspondence between the portion of the roadmap pathway and the curve within the score image by determining that pixels that are disposed in a given sequence in the additional extraluminal image correspond to respective pixels along the roadmap pathway, the corresponding pixels being disposed along the roadmap pathway in the same given sequence.

For some applications:
 the apparatus is for use with an endoluminal device configured to be placed inside the lumen,
 the computer processor is configured to acquire the at least one additional extraluminal image of the lumen by acquiring a second set of extraluminal images while the endoluminal device is disposed inside the lumen,
 the computer processor is configured to determine the transformation function for mapping between the location within the roadmap image and the location within the additional extraluminal image by determining respective transformation functions for mapping between locations within the roadmap image and locations within respective image belonging to the second set of extraluminal images, and
 the computer processor is configured, based upon the mapping, to determine locations of the endoluminal device in respective extraluminal images of the second set of extraluminal images with respect to the roadmap image.

For some applications, the computer processor is configured to determine locations of the endoluminal device in respective extraluminal images of the second set of extraluminal images with respect to the roadmap image by, in real-time with respect to acquisitions of the extraluminal images of the second set of extraluminal images, determining locations of the endoluminal device in respective extraluminal images of the second set of extraluminal images with respect to the roadmap image, and the computer processor is configured to generate the output by generating an output that is indicative of the determined real-time location of the endoluminal device with respect to the roadmap image.

For some applications:
 the endoluminal device includes a first endoluminal data-acquisition device configured to acquire a plurality of endoluminal data points while the endoluminal data-acquisition device is being moved through the lumen,
 the computer processor is configured, based upon determining locations of the endoluminal device in respective extraluminal images of the second set of extraluminal images with respect to the roadmap image, to co-register respective endoluminal data points to respective locations within the roadmap image, and
 the computer processor is configured to generate the output by generating an output based upon the co-registration of the endoluminal data points to the respective locations within the roadmap image.

For some applications, the endoluminal data-acquisition device includes an endoluminal imaging device that is configured to acquire a plurality of endoluminal images while the endoluminal imaging device is being moved through the lumen, and the computer processor is configured to co-register respective endoluminal data points to respective locations within the roadmap image by co-registering respective endoluminal images to respective locations within the roadmap image.

For some applications, the endoluminal data-acquisition device includes an endoluminal data-acquisition device that is configured to acquire functional data regarding the lumen, while the endoluminal data-acquisition device is being moved through the lumen, and co-registering respective endoluminal data points to respective locations within the roadmap image includes co-registering respective functional endoluminal data points to respective locations within the roadmap image.

For some applications, the computer processor is configured to generate the output based upon the co-registration, by generating a stack of endoluminal data points in which relative dispositions of endoluminal data points within the stack correspond to relative locations of the endoluminal data points with respect to the roadmap image.

There is further provided, in accordance with some applications of the present invention, a computer software product, for use with an extraluminal imaging device configured to acquire extraluminal images of a lumen of a body of a subject, and an output device, the computer software product including a non-transitory computer-readable medium in which program instructions are stored, which instructions, when read by a computer cause the computer to perform the steps of acquiring at least one first extraluminal image of the lumen, using the extraluminal imaging device; designating the at least one first extraluminal image as a roadmap image; designating, within the roadmap image, a roadmap pathway; acquiring at least one additional extraluminal image of the lumen, using the extraluminal imaging device; generating a score image, by applying a scoring function to at least some pixels within the additional extraluminal image, such that each of the pixels to which the scoring function is applied is designated a score that is indicative of an extent to which the pixel has a given characteristic; based upon the scores of at least some of the pixels to which the scoring function was applied, determining a correspondence between at least a portion of the roadmap pathway and a curve within the score image; and based upon the correspondence between the portion of the roadmap pathway and the curve within the score image, determining a transformation function for mapping between a location within the roadmap image and a location within the additional extraluminal image; and, in response thereto, generating an output on the output device.

The present invention will be more fully understood from the following detailed description of embodiments thereof, taken together with the drawings, in which:

BRIEF DESCRIPTION OF THE DRAWINGS

FIGS. 3A-C are flowcharts showing steps of a procedure that is performed by a computer processor in order to designate a parameter to be calculated, in accordance with some applications of the present invention;

FIG. 5 is a flowchart showing steps of a procedure that is performed by a computer processor in order to determine a location of a tip of a radiopaque portion of a wire within an extraluminal image of a blood vessel, in accordance with some applications of the present invention;

FIG. 7 is a flowchart showing steps of a procedure that is used to identify whether a given pixel within an image that contains an object corresponds to a portion of the object, in accordance with some applications of the present invention;

FIGS. 9A-B are schematic illustrations of regions of respective extra-luminal images, circular sampling regions of which are sampled around a pixel of the image, in accordance with some applications of the present invention;

FIG. 10 is a flowchart showing steps of a procedure that is used to determine a transformation function for mapping between a location within a roadmap image of a lumen and a location within a second image of the lumen, in accordance with some applications of the present invention.

DETAILED DESCRIPTION OF EMBODIMENTS

Figure 1:
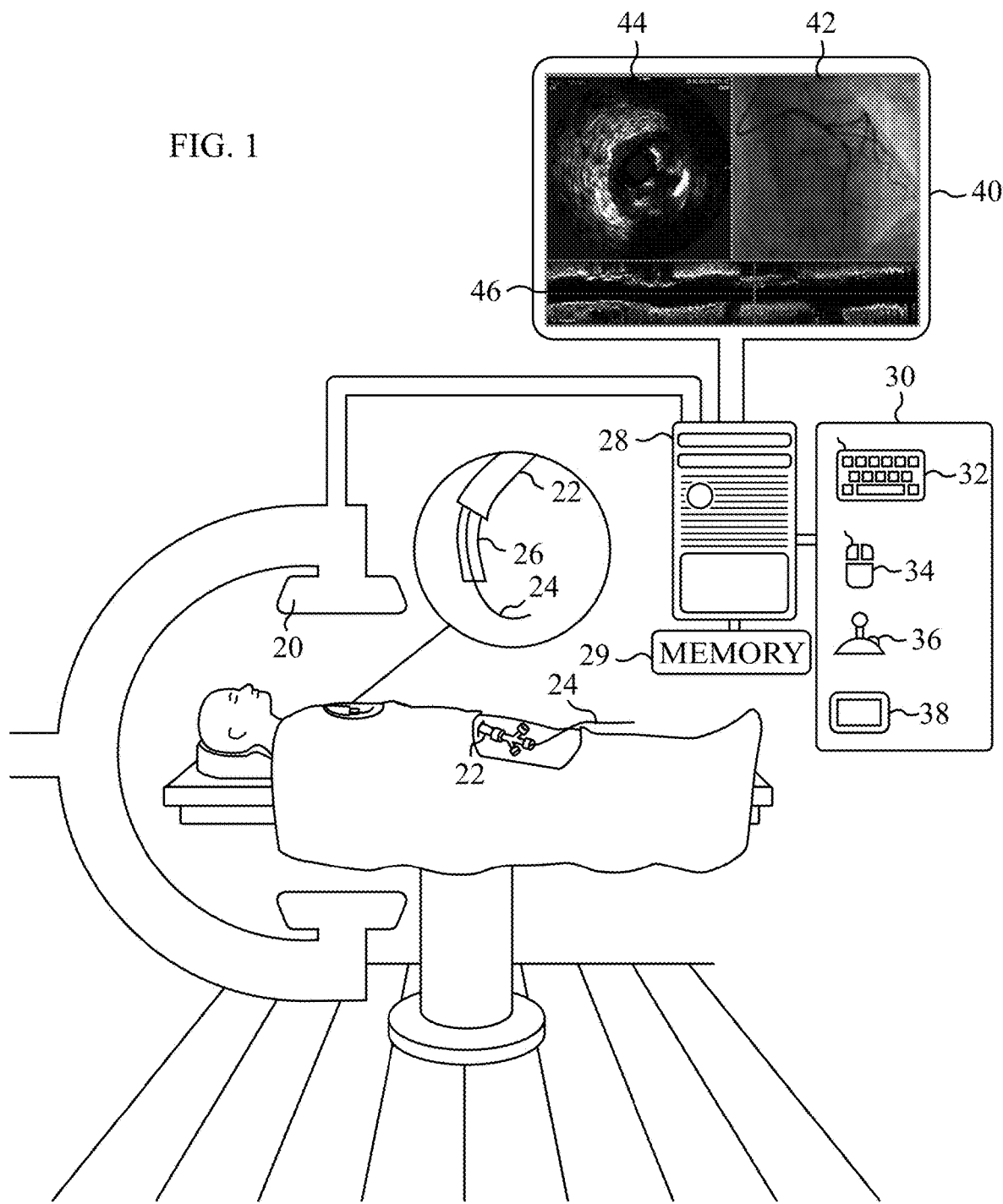
FIG. 1 is a schematic illustration of apparatus that is used in a catheterization laboratory, in accordance with some applications of the present invention.

The terms "medical tool," "tool", "device," and "probe" refer to any type of a diagnostic or therapeutic or other functional tool including, but not limited to, a cardiovascular catheter, a stent delivery, placement and/or retrieval tool, a balloon delivery and/or placement and/or retrieval tool, a valve delivery and/or repair and/or placement and/or retrieval tool, a graft delivery and/or placement and/or retrieval tool, a tool for the delivery and/or placement and/or retrieval of an implantable device or of parts of such device, an implantable device or parts thereof, a tool for closing a gap, a tool for closing a septal defect, a guide wire, a marker wire, a suturing tool, a clipping tool (such as a valve-leaflet-clipping tool), a biopsy tool, an aspiration tool, a navigational tool, a localization tool, a probe comprising one or more location sensors, a tissue characterization probe, a probe for the analysis of fluid, a measurement probe, an electrophysiological probe, a stimulation probe, an ablation tool, a tool for penetrating or opening partial or total occlusions in blood vessels, a drug or substance delivery tool, a chemotherapy tool, a photodynamic therapy tool, a brachytherapy tool, a local irradiation tool, a laser device, a tool for delivering energy, a tool for delivering markers or biomarkers, a tool for delivering biological glue, an irrigation device, a suction device, a ventilation device, a device for delivering and/or placing and/or retrieving a lead of an electrophysiological device, a lead of an electrophysiological device, a pacing device, a coronary sinus device, an imaging device, a sensing probe, a probe comprising an optical fiber, a robotic tool, a tool that is controlled remotely, an excision tool, a plaque excision tool (such as a plaque excision catheter), or any combination thereof The terms "image" and "imaging" refer to any type of medical images or imaging, typically resulting in the generation of a sequence of images and including, but not limited to, imaging using ionizing radiation, imaging using non-ionizing radiation, video, fluoroscopy, angiography, ultrasound, CT, MR, PET, PET-CT, CT angiography, SPECT, Gamma camera imaging, Optical Coherence Tomography (OCT), Near-Infra-Red Spectroscopy (NIRS), Vibration Response Imaging (VRI), optical imaging, infrared imaging, electrical mapping imaging, other forms of functional imaging, Focused Acoustic Computed Tomography (FACT), Optical Frequency Domain Imaging (OFDI), or any combination or fusion thereof. Examples of ultrasound imaging include Endo-Bronchial Ultrasound (EBUS), Trans-Thoracic Echo (TTE), Trans-Esophageal Echo (TEE), Intra-Vascular Ultrasound (IVUS), Intra-Cardiac Ultrasound (ICE), or any combination thereof.

The term "contrast agent," when used in reference to its application in conjunction with imaging, refers to any substance that is used to highlight, and/or enhance in another manner, the anatomical structure, functioning, and/or composition of a bodily organ while the organ is being imaged.

The term "stabilized," when used in the context of displayed images, means a display of a series of images in a manner such that periodic, cyclical, and/or other motion of the body organ(s) being imaged, and/or of a medical tool being observed, is partially or fully reduced, with respect to the entire image frame, or at least a portion thereof.

The term "automatic," when used for describing the generation and utilization of the roadmap, means "without necessitating user intervention or interaction." (Such interaction or intervention may still however be optional in some cases.)

The term "real-time" means without a noticeable delay.

The term "near real-time" means with a short noticeable delay (such as approximately one or two motion cycles of the applicable organ, and, in the case of procedures relating to organs or vessels the motion of which are primarily a result of the cardiac cycle, less than two seconds).

The term "on-line," when used in reference to image processing, or to measurements being made on images, means that the image processing is performed, and/or the measurements are made, intra-procedurally, in real-time or near real-time.

Reference is now made to FIG. 1, which is a schematic illustration of apparatus that is used in a catheterization laboratory, in accordance with some applications of the present invention. Typically, a subject is imaged using an extraluminal imaging device (i.e., an extraluminal image-acquisition device) 20, which may include a fluoroscope that acquires fluoroscopic images under regular mode and/or under angiographic mode, while there is a presence of contrast agent in the blood vessels of the subject that are being imaged. For some applications, the imaging device performs fluoroscopy, CT, MR, PET, SPECT, ultrasound, or any combination thereof.

FIG. 1 additionally shows a guide catheter 22 that has been inserted into blood vessels of the subject (e.g., coronary arteries of the subject) over a guidewire 24. An endoluminal medical device 26 has been inserted into a blood vessel of the subject (e.g., into a coronary artery of the subject) through the guide catheter and over the guidewire. A computer processor 28 typically receives inputs from the imaging device. The computer processor communicates with a memory 29. Via a user interface 30, a user (e.g., a physician and/or a catheterization laboratory technician) sends instructions to the computer processor. For some applications, the user interface includes a keyboard 32, a mouse 34, a joystick 36, a touchscreen device 38 (such as a smartphone or a tablet computer), a touchpad, a trackball, a voice-command interface, and/or other types of user interfaces that are known in the art. Typically, the computer processor generates an output using an output device 40. Further typically, the output device includes a display, such as a monitor (as shown in FIG. 1), and the output includes an output that is displayed on the display. For some applications, the display includes a head-up display and/or a head-mounted display, such as Google Glass®. For some applications, the processor generates an output on a different type of visual, text, graphics, tactile, audio, and/or video output device, e.g., speakers, headphones, a smartphone, or a tablet computer. For some applications, user interface 30 acts as both an input device and an output device. For some applications, the processor generates an output on a computer-readable medium (e.g., a non-transitory computer-readable medium), such as a disk, or a portable USB drive.

It is noted that, for some applications, more than one processor is used. For some applications, more than one extraluminal imaging device is used with processor 28. For example, a first extraluminal imaging device may be used to acquire a first set of extraluminal images, and a second extraluminal imaging device may be used to acquire a second set of extraluminal images.

For some applications, endoluminal medical device 26 includes an endoluminal data-acquisition device that is configured to acquire data (e.g., functional data or images) from inside the subject's blood vessels. For some applications, the endoluminal data-acquisition device is an imaging probe. For some applications, the imaging probe is an IVUS probe, an EBUS probe, a different type of ultrasound probe, an OCT probe, an NIRS probe, an MR probe, a FACT probe, an OFDI probe, or any combination thereof. For some applications, the endoluminal data-acquisition device performs additional functions. For example, the endoluminal data-acquisition device may comprise a probe, such as the VIBE™ RX Vascular Imaging Balloon Catheter, marketed by Volcano Corporation (San Diego, USA), that includes both IVUS and coronary balloon functionalities. For some applications, the endoluminal data-acquisition device acquires data in a form other than images. For example, the data may include data related to pressure, flow, temperature, electrical activity, oxygenation, biochemical composition, or any combination thereof. For some applications, and typically when data are acquired with respect to a coronary vessel, the endoluminal data-acquisition device is a Fractional Flow Reserve (FFR) probe, and/or an instantaneous wave-free ratio (iFR) probe. For some applications, FFR and/or iFR measurements are determined by performing image-processing on extraluminal images, and the derived FFR and/or iFR measurements are co-registered with endoluminal images of the lumen, using techniques described herein. For some applications, FFR and/or iFR measurements are determined by performing image-processing on endoluminal images, and the derived FFR and/or iFR measurements are co-registered with extraluminal images of the lumen, using techniques described herein. For some applications, endoluminal images are co-registered with extraluminal images of the lumen, using techniques described herein, and FFR and/or iFR measurements are determined by performing image-processing on the co-registered images.

For some applications, endoluminal medical device 26 includes an endoluminal therapeutic device that is positioned and/or deployed at an anatomical feature that requires or potentially requires treatment, such as a partial or total occlusion, a native valve, an aneurism, a dissection, a malformation, a septal defect, a mass suspected of being malignant, a mass suspected of being inflammatory, etc. For example, the endoluminal therapeutic device may include a balloon (e.g., an angioplasty balloon), a stent, a valve, and/or a wire (e.g., a guide wire).

For some applications, apparatus and methods described herein are used with an endoluminal therapeutic device that is positioned and/or deployed at an implantation site of a previously-implanted device such as a stent, a graft or a replacement valve. The endoluminal data are determined at, and/or in the vicinity of, the implantation site. For example, the techniques described herein may be used during the placement of a new prosthetic aortic valve at the site of (e.g., inside) a previously implanted prosthetic aortic valve that is no longer functioning.

For some applications, apparatus and methods described herein are used with an endoluminal therapeutic device that is positioned and/or deployed at a defined location relative to a previously-implanted device such as a stent, a graft or a replacement valve. The endoluminal data are determined at and in the vicinity of the defined location. For example, the techniques described herein may be used during the placement of a coronary stent such that the new stent overlaps with or is adjacent to a previously-implanted stent, in order to treat a long lesion and/or a lesion that has diffused along a coronary artery.

For some applications, output device 40 is a display that is configured to display an extraluminal image 42 of a blood vessel (e.g., a fluoroscopic image), an endoluminal image of a blood vessel 44 (e.g., an IVUS image), and or a stack 46 of cross-sections of endoluminal images (e.g., a stack of IVUS images).

Figure 2A:
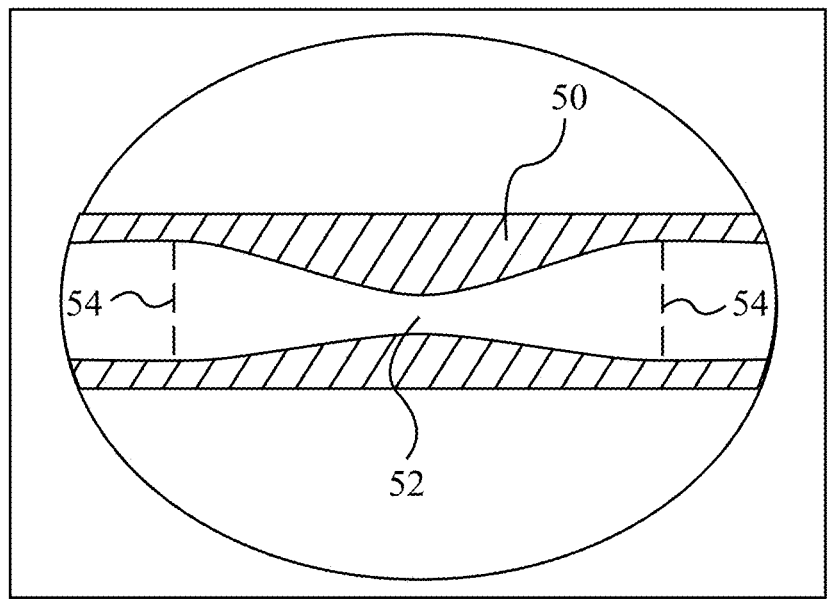
FIG. 2A is a schematic illustration of an extraluminal image of a blood vessel that has lesion, in accordance with some applications of the present invention.
Figure 2B:
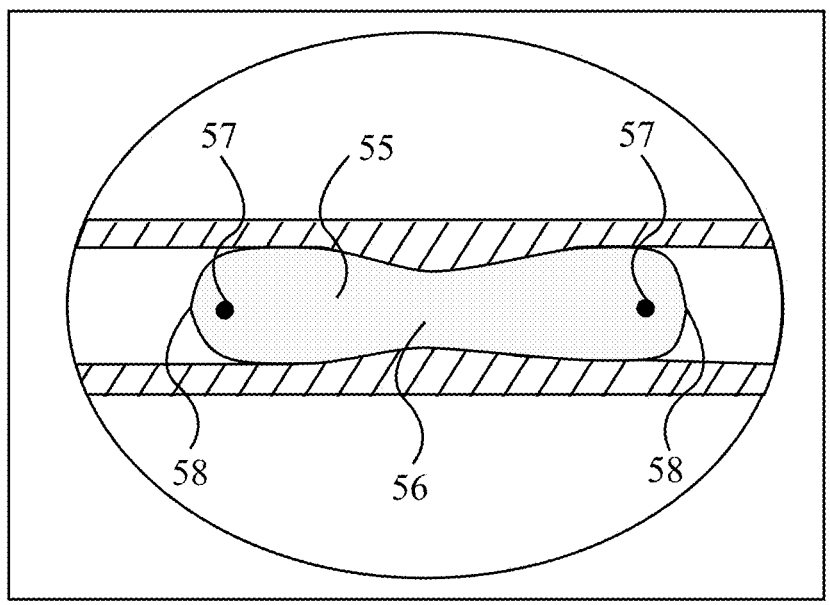
FIG. 2B is a schematic illustration of an extraluminal image of an angioplasty balloon that has been maximally inflated inside a blood vessel, such as to treat an occlusion, in accordance with some applications of the present invention.
Figure 2D:
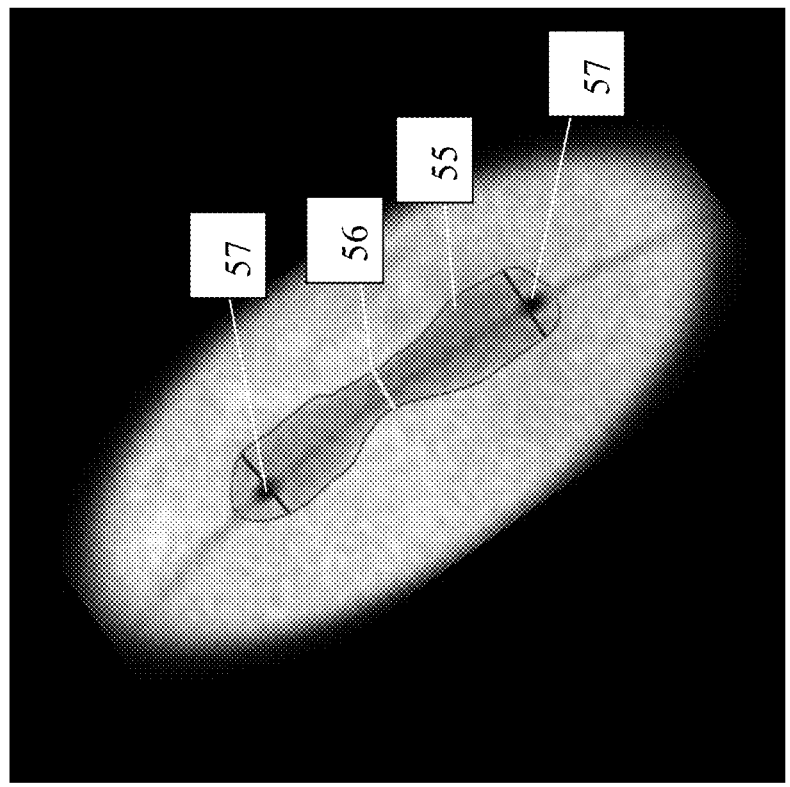
FIGS. 2C-D are extraluminal images of an angioplasty balloon that has been maximally inflated inside a blood vessel, such as to treat an occlusion, in accordance with some applications of the present invention.
Figure 2C:
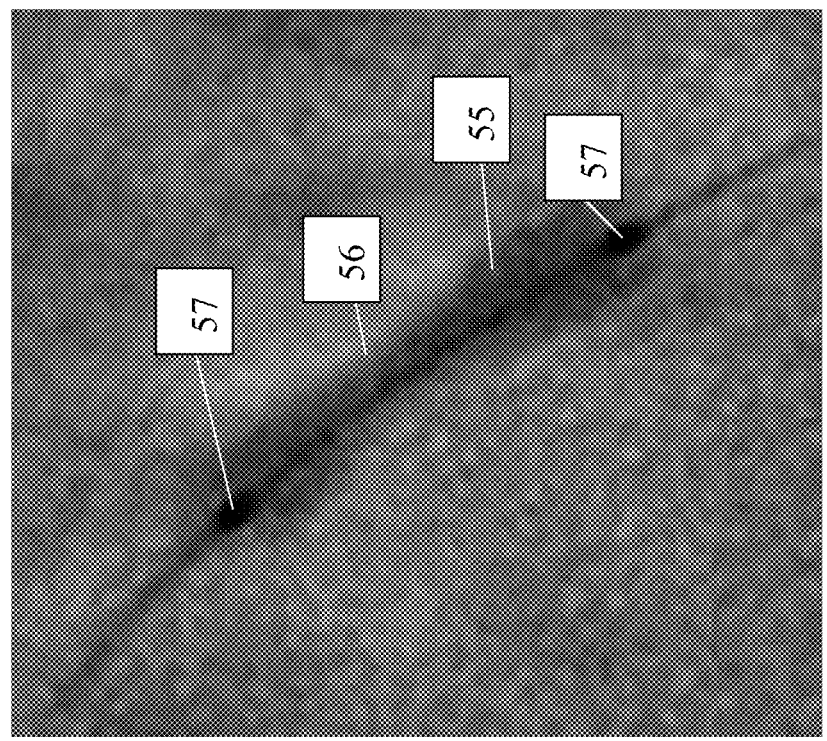

Reference is now made to FIGS. 2A and 2B, which are schematic illustrations of extraluminal images of a blood vessel, in accordance with some applications of the present invention. Reference is also made to FIGS. 2C and 2D, which are images of a balloon disposed inside an artery, in accordance with some applications of the present invention. FIG. 2D shows an enhanced version of the image shown in FIG. 2C, with the edge lines of the balloon marked upon the image.

FIG. 2A is a schematic illustration of an extraluminal image of a blood vessel 50 (such as a coronary artery) that has lesion, e.g., a partial occlusion 52, in accordance with some applications of the present invention. Typically, in the absence of a device inside the vessel, in response to a user indicating a location of the lesion (e.g., by the user indicating a single point in the vicinity of the lesion in the image), the processor automatically performs quantitative vessel analysis on the blood vessel in the vicinity of the lesion. Typically techniques such as those described in US 2012/ 0230565 to Steinberg, and/or US 2010/0222671 to Cohen, both of which are incorporated herein by reference, are used for performing quantitative vessel analysis in the vicinity of the lesion. For example, using an input device (e.g., user interface 30), the user may designate the location (for example, by clicking a single click or a plurality of clicks at or near the location using the input device), and in response to the user designating the location, the system automatically detects a lesion in the vicinity. For example, the system may identify edge lines and the reference diameters 54 of the lesion. The reference diameters of a lesion are typically the diameters of the vessel at the longitudinal extremities of the lesion (the longitudinal extremities also being known as "healthy shoulders," or "reference arteries" to those skilled in the art). For some applications, the reference diameters are the broadest location within the section of the blood vessel that is analyzed. In response to detecting the lesion, quantitative vessel analysis is performed with respect to the lesion. For some applications, the lesion is graphically indicated, for example, by highlighting or coloring the section of the vessel that is determined to be the lesion. For some applications, measurements such as lesion length, the diameter of the vessel at each point along the centerline, and/or minimum lumen diameter is determined in the vicinity of the lesion. For some applications, the level of occlusion (which is typically provided as a percentage) at the minimum lumen diameter is determined by comparing the diameter of the vessel at that point, to the diameter of the vessel at reference points of the vessel.

Typically, the quantitative vessel analysis is performed by determining the locations of vessel centerlines and/or edge lines, for example, using techniques such as those described in US 2012/0230565 to Steinberg, and/or US 2010/0222671 to Cohen, both of which are incorporated herein by reference. For some applications, a lesion is automatically detected in accordance with the following procedure.

Scan lines are generated perpendicular to the centerline of a segment of the vessel that is sampled. The image is resampled along the scan lines. Corresponding gray-level values are stored as columns of a rectangular matrix M, thereby resampling the segment of the vessel as a straightened vessel segment. For the straightened vessel segment, optimum upper and lower paths are determined (with respect to the middle row of M), which connect the first and last columns of M. The optimization criterion takes into account the changes in gray-level along columns of M, and the paths' slopes. The vessel edge lines are obtained via back projection of upper and lower optimal paths on the original image.

A shortest path algorithm (e.g., as described in an article by Dijkstra, entitled "A Note on Two Problems in Connexion with Graphs" (Numerische Mathematik 1, 269-271, 1959), which is incorporated herein by reference) is used in order to avoid irregularities, such as small gaps and loops, in the edge lines. For some applications, the centerline is corrected based upon the detected edge lines, and new scan lines are constructed. For each new scan line, vessel diameter is defined as a distance between the two points where the scan line intersects vessel boundaries.

FIG. 2B is a schematic illustration of an extraluminal image of an angioplasty balloon 55 (e.g., a compliant angioplasty balloon) that has been maximally inflated inside the blood vessel (i.e., inflated to the maximum pressure to which the balloon can safely be inflated in such as vessel), such as to treat the occlusion, in accordance with some applications of the present invention. FIGS. 2C and 2D are actual images of angioplasty balloon 55, the balloon having been inflated inside an artery at a partial occlusion, in accordance with some applications of the present invention. FIG. 2D shows an enhanced version of the image shown in FIG. 2C, with the edge lines of the balloon marked upon the image. As shown in FIGS. 2B-D, in some cases, even after the balloon is maximally inflated, the occlusion is not fully treated, but maintains what is known as a residual waist 56. It is typically desirable to be able to calculate the diameter of the vessel at the residual waist of the occlusion.

For some applications, if the processor uses the algorithm described hereinabove for performing quantitative vessel analysis on the vessel with the balloon inside, the processor may identify one or both ends 58 of the balloon as being the location of the minimal lumen diameter, since the system may not differentiate between edge lines of the vessel and edge lines of the balloon. Therefore, for some applications, in order to avoid the processor identifying one or both ends 58 of the balloon as being the location of the minimal lumen diameter, the processor determines that the balloon is present within the blood vessel. The processor determines a parameter of the vessel responsively to determining the presence of the balloon within the vessel, for example, in accordance with the techniques described hereinbelow with reference to FIGS. 3A-C.

Figure 3A:
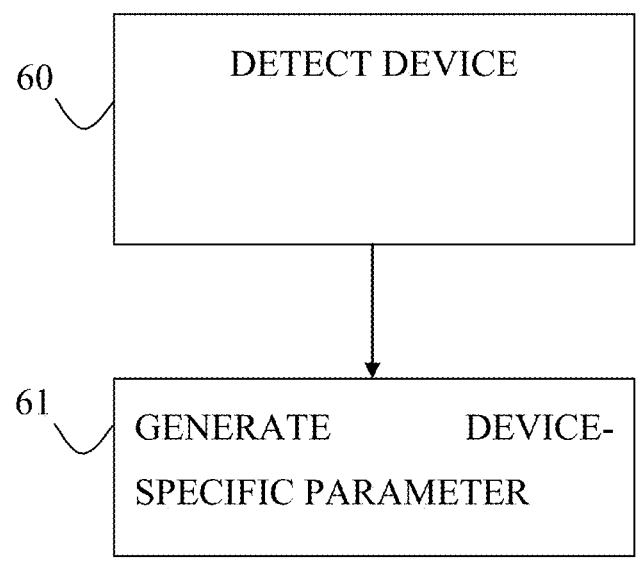
Figure 3C:
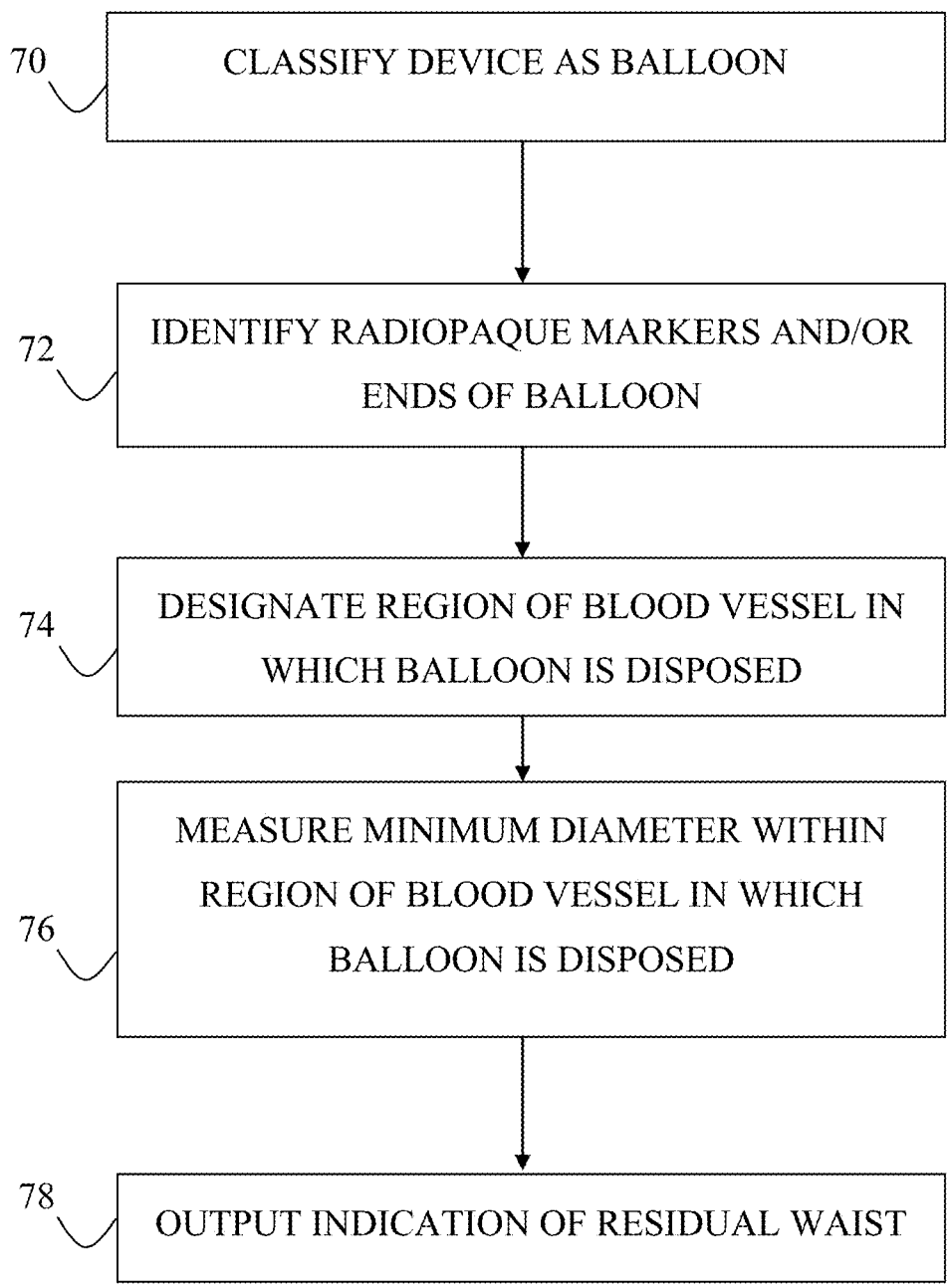

Reference is now made to FIGS. 3A-C, which are flowcharts showing steps of a procedure that is performed by computer processor 28, in accordance with some applications of the present invention.

As shown in FIG. 3A, for some applications, the processor detects a device (step 60). Typically, the processor detects the device within an image of a portion of the subject's body, as described hereinbelow. In response to detecting the device, the processor generates as an output (e.g., on output device 40) a device-specific parameter (step 61), e.g., using the techniques described hereinbelow.

As shown in FIG. 3B, for some applications, the processor determines a presence of a device within a blood vessel within an image (step 63), and classifies the device as a given type of device (step 64), such as a balloon. In response to determining the classification of the device, the processor designates a parameter to be calculated (step 65). It is noted that, for some applications, the determination of the presence of a device within a blood vessel within an image (step 63), and the classification of the device as a given type of device (step 64) are performed simultaneously, or in the reverse order to that shown in FIG. 3B. For some applications, the user indicates that a given type of device (e.g., a balloon) is currently being inserted into the blood vessel (or is going to be inserted, or has been inserted, into the blood vessel), via user interface 30. Based upon the indication from the user, the processor automatically determines when the device is present inside the blood vessel, and the proceeds to step 65.

Subsequent to designating the parameter to be calculated (step 65), the processor calculates the designated parameter (step 66) and generates an output in response thereto (step 68). For example, in the example of angioplasty balloon 55, shown in FIG. 2B, in response to classifying the device as a balloon, the processor may designate as the parameter to be calculated, the minimum diameter of the vessel between the two ends of the balloon, and/or between two radiopaque markers 57 (FIG. 2B) of the balloon, which corresponds to the residual waist of the occlusion.

As shown in FIG. 3C, for some applications, in order to calculate the residual waist of the occlusion, in response to classifying the device as a balloon (step 70), the processor identifies locations of ends of the balloon and/or locations of radiopaque balloon markers 57 (step 72). Typically, the processor identifies balloon markers using image processing techniques, e.g., using techniques described herein for identifying balloon markers, and/or using techniques as described in US 2012/0230565 to Steinberg, and/or US 2010/0222671 to Cohen, both of which are incorporated herein by reference. For some applications, balloon markers are detected using the technique described hereinbelow with reference to FIG. 7. For some applications, the processor determines locations of ends of the balloon, e.g., by detecting a location within the image in which there are generally straight edge lines (corresponding to the vessel edge lines), and within the straight edge lines there are tapered pairs of edge lines (corresponding to the tapered edges of the balloon).

The processor designates as a region of the vessel in which the balloon is disposed, a region of the vessel that is between the radiopaque markers of the balloon, and/or a region of the vessel that is between the tapered pairs of edge lines at each longitudinal end of the balloon (step 74). The processor then determines the minimum lumen diameter within the region of the vessel in which the balloon is disposed (step 76). The minimum lumen diameter within the region of the vessel in which the balloon is disposed is the residual waist of the occlusion. The processor then generates an output that is indicative of the calculated residual waist (step 78).

For some applications, the detection and/or classification of the device (steps 63 and 64 of FIG. 3B) are performed automatically by the processor using one or more algorithms described herein. For example, the processor may use automatic image-processing techniques to determine the presence of and/or the classification of the device. For some applications, the processor uses a machine-learning algorithm in order to automatically classify the device. For such applications, the processor compares an appearance of and/or characteristics of the detected device to machine-learned appearances and characteristics. For example, one or more of the following machine learning techniques may be used: Support Vector Machine (SVM), Deep Believe Networks, Neural Networks, and/or Random Decision Forest. Alternatively or additionally, the processor compares an appearance of and/or characteristics of a region of the image to machine-learned characteristics and appearances. Further alternatively or additionally, the processor receives an input from a user (typically via user interface 30) that is indicative of the presence of the device inside the vessel, and/or the classification of the device. As described hereinabove, for some applications, the user indicates that a given type of device (e.g., a balloon) is currently being inserted into the blood vessel (or is going to be inserted, or has been inserted, into the blood vessel), via user interface 30. Based upon the indication from the user, the processor automatically determines when the device is present inside the blood vessel, and then proceeds to step 65.

For some applications, the processor designates the parameter to be calculated (step 65 of FIG. 3B), using one or more algorithms described herein. For some applications, the processor designates the parameter to be calculated by designating a parameter of the blood vessel to be calculated. In accordance with some applications, the parameter of the blood vessel is a dimension of the blood vessel and/or a functional parameter of the blood vessel. For example, in response to classifying the device as a stent, the processor may designate, as the parameter to be calculated, the minimum lumen diameter of the blood vessel within a region of the blood vessel in which the stent is disposed, in order to determine the minimum lumen diameter of the vessel in presence of the stent. For some applications, the stent is disposed around a balloon, and the processor determines the region of the blood vessel in which the stent is disposed by determining locations of the radiopaque markers of the balloon around which the stent is disposed.

Alternatively or additionally, in response to classifying the device as a stent, the processor may designate functional flow reserve (or another luminal flow-related index) at the location of the stent as the parameter to be calculated, in order to determine the effect of the stent on the functional flow reserve (or the other luminal flow-related index) of the vessel. For some applications, the processor designates the parameter to be calculated by designating a parameter of the device to be calculated. For example, in response to classifying the device as a stent, the processor may designate a maximum diameter of the stent, or a minimum diameter of the stent as the parameter to be calculated. For some applications, the stent is disposed around a balloon, and the processor determines the region of the blood vessel in which the stent is disposed by determining locations of the radiopaque markers of the balloon around which the stent is disposed.

For some applications, the processor designates an event and designates the parameter to be calculated by designating a parameter to be calculated at the occurrence of the event. For example, in the example described with reference to FIGS. 2B and 3C, the processor may designate maximum inflation of the balloon as the event, and the processor may determine the residual waist of the occlusion at the occurrence of maximal balloon inflation. For some applications, the processor automatically detects the occurrence of the designated event, e.g., using automatic image-processing techniques.

Typically, the parameter is calculated (step 66 of FIG. 3B), using one or more algorithms described herein. For some applications, the parameter is calculated by analyzing the image using automatic image-processing techniques. For example, dimensions of the vessel and/or the device may be calculated using techniques as described in US 2012/0230565 to Steinberg, and/or US 2010/0222671 to Cohen, both of which are incorporated herein by reference. Alternatively or additionally, functional parameters may be calculated automatically, for example, using techniques as described in WO 14/002095 to Tolkowsky, which is incorporated herein by reference.

For some applications, in order to calculate the parameter, vessel and/or device edge lines are automatically identified, using techniques described herein. For example, scan lines may be generated perpendicular to the centerline of a segment of the vessel that is sampled. The image is resampled along the scan lines. Corresponding gray-level values are stored as columns of a rectangular matrix M, thereby resampling the segment of the vessel as a straightened vessel segment. For the straightened vessel segment, optimum upper and lower paths are determined (with respect to the middle row of M), which connect the first and last columns of M. The optimization criterion takes into account the changes in gray-level along columns of M, and the paths' slopes. The vessel edge lines are obtained via back projection of upper and lower optimal paths on the original image.

A shortest path algorithm (e.g., as described in an article by Dijkstra, entitled "A Note on Two Problems in Connexion with Graphs" (Numerische Mathematik 1, 269-271, 1959), which is incorporated herein by reference) is used in order to avoid irregularities, such as small gaps and loops, in the edge lines. For some applications, the centerline is corrected based upon the detected edge lines, and new scan lines are constructed. For each new scan line, vessel and/or device diameter is defined as a distance between the two points where the scan line intersects edge lines.

For some applications, the techniques described herein are performed with respect to other devices, and/or with respect to other portions of a subject's body to those described hereinabove.

For some applications, the techniques described herein are used in order to determine a parameter that relates to a hole-closure device. For example, the hole-closure device may be an atrial septal defect closure device, a left-atrial appendage closure device, and/or a hole-closure device that is used to close a surgically-created hole, such as in the apex of the subject's heart, and/or in a peripheral blood vessel, such as the femoral vein or the femoral artery. In response to determining the presence of a device within an image of a portion of the subject's body, and classifying the device as a hole-closure device, computer processor 28 may determine the maximum diameter of the hole-closure device, subsequent to the deployment of the hole-closure device. Alternatively or additionally, the techniques described herein may be used in order to determine a parameter that relates to an implantable valve (such as a prosthetic aortic valve, and/or a prosthetic mitral valve), e.g., the maximum diameter of the valve, subsequent to deployment of the valve. Further alternatively or additionally, the techniques described herein may be used in order to determine a parameter that relates to a blood vessel filter (e.g., a vena cava filter, such as the Crux® Vena Cava Filter, manufactured by Volcano Corporation (CA, USA)), e.g., the maximum diameter of the filter, subsequent to deployment of the filter within a blood vessel.

For some applications, the techniques described herein are used in order to determine a parameter that is related to a previously-implanted device (such as a stent, a graft or a replacement valve that was implanted prior to the present procedure being performed (e.g., at least one day prior to the present procedure being performed), in response to determining a presence of the previously-implanted device within an image of a portion of the subject's body, and in response to classifying the previously-implanted device as a given type of device.

Figure 4:
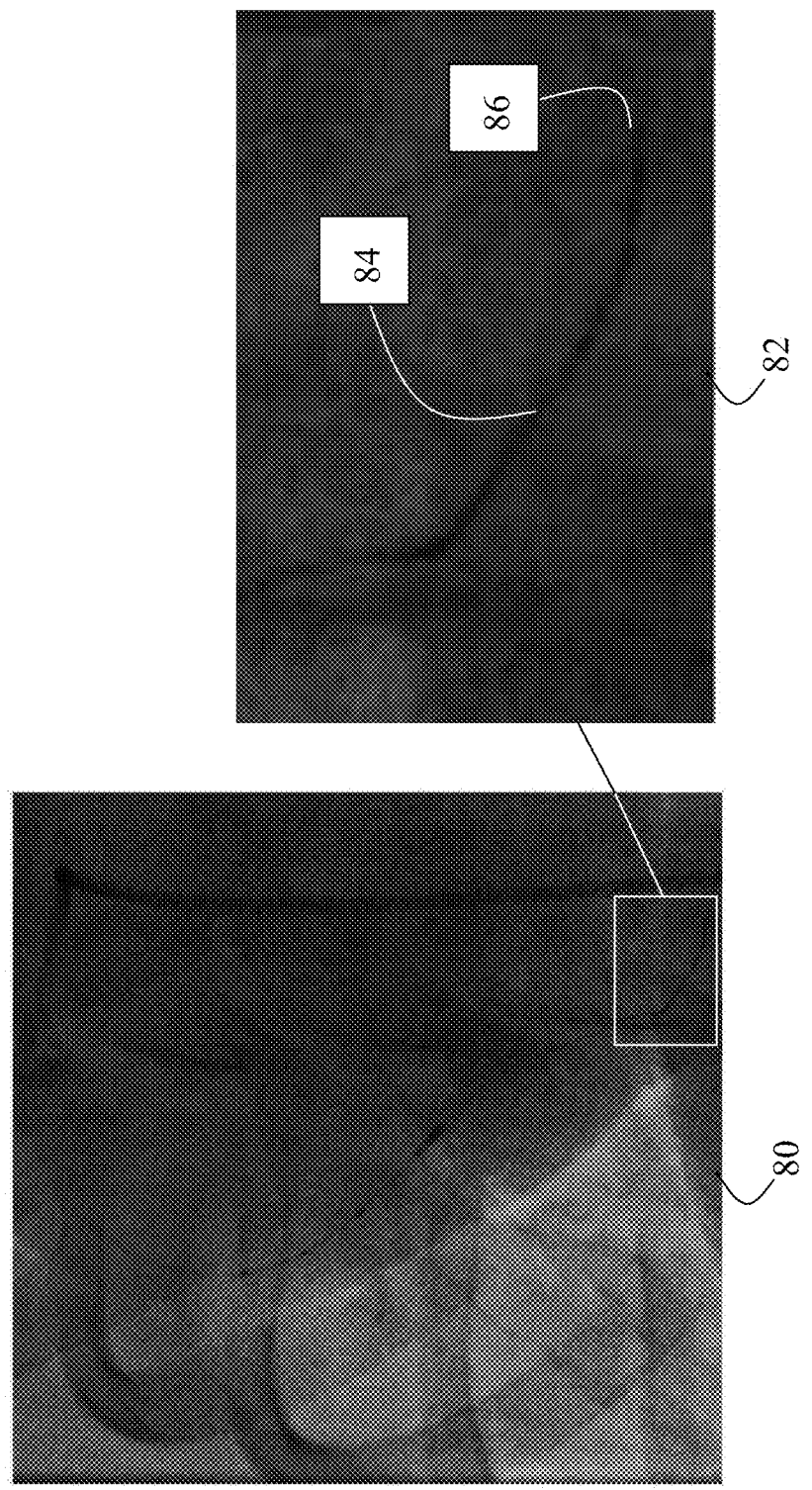
FIG. 4 is an image of a blood vessel, a wire (e.g., a guidewire) being disposed inside the blood vessel, in accordance with some applications of the present invention.

Reference is now made to FIG. 4, which is an image of a blood vessel, a wire (e.g., a guidewire) being disposed inside the blood vessel, in accordance with some applications of the present invention. Right frame 82 of FIG. 4A is an enlargement of a portion of left frame 80, the enlarged portion containing an image of a radiopaque end portion 84 of the guidewire. For some applications, a tip 86 of the radiopaque portion of the guidewire is automatically identified, using techniques described herein. Typically, as may be observed in FIG. 4, in a fluoroscopic image (or a different extraluminal image) of a blood vessel, there are darkened pixels within the image due to noise. Therefore, typically it is not possible to distinguish pixels that correspond to the radiopaque portion of the guidewire from surrounding pixels simply by analyzing the intensities of respective pixels. For some applications, computer processor 28 automatically determines a location of a tip of a radiopaque portion of the wire within the image using a technique as described with reference to FIG. 5.

Reference is now made to FIG. 5, which is a flowchart showing steps of a procedure that is performed by computer processor 28 in order to determine a location of a tip of a radiopaque portion of the wire within an extraluminal image of a blood vessel, in accordance with some applications of the present invention.

For each pixel within at least a portion of the image, a wireness measure of the pixel is determined (step 90). (It is noted that as used herein, the term "pixel" should not be interpreted to be limited to the smallest controllable element of the picture represented on the screen. Rather, as used herein, the term "pixel" should be interpreted to mean a set of one or more such elements.) For some applications, wireness measures are determined for pixels within the entire image. Alternatively, wireness measures of pixels within only a portion of the image are determined. For example, wireness measures of pixels within a region of the image in which the radiopaque portion of the wire is expected to be disposed (e.g., based on locations of other features within the image) may be sampled. Alternatively or additionally, the processor may receive an input from the user indicating a region of the image in which the radiopaque portion of the wire is expected to be disposed.

The wireness measure is a measure of the extent to which each of the pixels has a wire-like characteristic. For some applications, the wireness measure of the pixel is determined using one or more algorithms described herein. Typically, for each of the selected pixels, the wireness measure is determined, by measuring an extent to which the pixel, together with other pixels within the image, forms part of a long, thin set of pixels having a given characteristic, such as darkness, brightness, and/or a different characteristic (i.e., a wireness-indicating characteristic). Typically, the wireness measure is indicative of the pixel, together with the other pixels within the set, corresponding to the wire.

For some applications, generally similar techniques to those described in US 2012/0230565 to Steinberg, and/or US 2010/0222671 to Cohen, both of which are incorporated herein by reference, for determining a vesselness measure of a pixel are used for determining the wireness measure of a pixel. For example, wireness may be determined by means of a Hessian filter, such as the filter described in the article by Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137), which is incorporated herein by reference, and/or by means of a filter that performs enhancement and/or detection and/or segmentation of curvilinear structures. For some applications, a filter is used that is similar to a Frangi filter, but that differs from a Frangi filter (a) in that wireness is a homogeneous function, and/or (b) in the multipliers employed for the normalization of scales.

For some applications, the wireness measure of a pixel is obtained by determining the extent to which the gradient of the pixel is orthogonal to the eigenvector of the Hessian matrix corresponding to the highest eigenvalue. For some applications, the determination is assisted by a voting function applied to pixels that are adjacent to those pixels that are eventually determined to constitute the wire itself.

For some applications, thresholding is applied to image pixels by means of hysteresis. For example, pixels the wireness values of which fall below the high threshold of the hysteresis, but yet above the low threshold of the hysteresis, are incorporated into the set of pixels if they are contiguous with pixels that fall at or above the high threshold of the hysteresis.

For some applications, the pixels which form the aforementioned set are determined by means of morphological operations. For example, such morphological operations may include the skeletonization of a thresholded vesselness image. For some applications, the threshold applied is adaptive according to the specific region in the image.

For some applications, machine-learning techniques are used to determine wireness measures of the pixels.

In the next step of the procedure, for each pixel within at least the portion of the image, an intensity of the pixel is determined (step 92). It is noted that, for some applications, steps 90 and 92 are performed in the reverse order to that shown in the flowchart in FIG. 5.

Subsequent to the wireness measures and the intensities of the pixels within the portion of the image having been determined, computer processor 28 designates a first sampling region within the portion of the image (step 94). For some applications, the first sampling region is designated in accordance with one or more algorithms described herein. For example, the sampling region may include a single pixel, or a plurality of pixels. The first sampling region may be generated randomly, and/or in response to an input from a user. For some applications, the processor designates the first sampling region by designating a sampling region in which the tip of the guidewire is likely to be disposed. For example, the processor may designate the first sampling region by designating one or more regions that have high values of the wireness measure. Alternatively or additionally, the processor may designate the first sampling region in response to determining that a region of the image is likely to contain the tip of the wire, based upon machine-learning analysis of the image.

For some applications, step 94 is performed before steps 90 and 92, and steps 90 and 92 are only performed on the designated sampling region.

The processor determines whether, within the first sampling region, there is at least one pixel, at which there is a change in the wireness measure, by more than a threshold amount, relative to the value of the wireness measure of at least some of the set of pixels having the wireness-indicating characteristic (step 96). For some applications, the processor performs step 96 using one or more algorithms described herein. For example, by way of illustration, the processor may determine that from one pixel to an adjacent pixel there is a decrease in the wireness measure that exceeds a threshold percentage decrease. Or, the processor may determine that at least one pixel has a wireness measure that is lower than the mean wireness measure of all of the pixels belonging to the set of pixels, by more than a threshold percentage.

For some applications, within the designated region, the processor determines the local directionality of the set of pixels that have the wireness-indicating characteristic. The processor determines, along that direction, whether there is at least one pixel at which there is a change in the wireness measure by more than a threshold amount, relative to at least some of the pixels that belong to the set of pixels that have the wireness-indicating characteristic.

In response to determining that there is not a change in the wireness measure at at least one pixel that exceeds the threshold, within the first sampling region, the processor proceeds to the next sampling region (step 98), and step 96 is repeated at the second sampling region. The second sampling region is typically selected in a generally similar manner to the selection of the first sampling region, and/or based upon a spatial relationship to the first sampling region. In response to determining that the change in the wireness measure at at least one pixel within a sampling region does exceed the threshold, the processor then determines whether, at the at least one pixel, there is a change, by more than a threshold amount, in the intensity of the pixel relative to the value of the intensity of at least some of the set of pixels having the wireness-indicating characteristic (step 100). For some applications, the processor performs step 100 using one or more algorithms described herein. For example, by way of illustration, the processor may determine that from one of the pixels to an adjacent pixel there is an increase in intensity that exceeds a threshold percentage increase. Or, the processor may determine that one of the pixels has an intensity that exceeds the mean intensity of all of the pixels belonging to the set of pixels, by more than a threshold percentage.

For some applications, within the designated region, the processor determines the local directionality of the set of pixels that have the wireness-indicating characteristic. The processor determines, along that direction, whether there is at least one pixel at which there is a change in intensity by more than a threshold amount, relative to at least some of the pixels that belong to the set of pixels that have the wireness-indicating characteristic.

In response to determining that there is not a change in the intensity at at least one pixel that exceeds the threshold, within the current sampling region, the processor proceeds to the next sampling region (step 98), and step 96 is repeated at the next sampling region. In response to determining that the change in intensity at at least one pixel within the current sampling region does exceed the threshold, it is determined that the tip of the radiopaque portion of the wire is disposed within the current sampling region (step 102). An output is generated in response to the determined location of the tip of the radiopaque portion of the wire within the image.

It is noted that, for some applications, steps 96 and 100 are performed in the reverse order, the processor first determining whether there is a change in the intensity at at least one pixel by more than a threshold amount, and, subsequently, determining whether there is a change in the wireness measure at the at least one pixel by more than the threshold amount.

Typically, an output is generated by computer processor 28 in response to the determined location of the tip of the radiopaque portion of the wire within the image. For some applications, the processor determines locations of both of the tips of the radiopaque portion of the wire, and thereby determines the location of the radiopaque portion of the wire, and/or the center of the radiopaque portion of the wire within the image. The output is generated in response to the determined location of the radiopaque portion of the wire, and/or in response to the determined location of the center of the radiopaque portion of the wire within the image.

For some applications, in response to determining the location of the tip of the radiopaque portion of the wire within a given image, the processor aligns the image with a second image, by aligning the radiopaque portions of the wires in each of the images with one another. In accordance with respective applications, the aligned images may be displayed in an image stream in which the images are aligned with one another, and/or a composite image may be generated based upon the alignment of the image and the second image. For example, the processor may average the image and the second image, subsequent to aligning the images with one another. In general, the identification of the location of the tip of the radiopaque portion of the wire within a given image may be used to perform any of the image stabilization and/or enhancement techniques that are described in any one of US 2008/0221440 to Iddan, US 2012/0230565 to Steinberg, and US 2010/0222671 to Cohen, all of which applications are incorporated herein by reference.

For some applications, identification of the location of the tip of the radiopaque portion of the wire within a given image may be used to facilitate the determination of the location of an endoluminal device within the lumen, for example, in accordance with techniques described in US 2012/0004537 to Tolkowsky, US 2014/0094691 to Steinberg, and/or WO 13/175472 to Steinberg, which are incorporated herein by reference. For example, the location within the blood vessel at which one or more endoluminal data points were acquired by the endoluminal data-acquisition device (e.g., an endoluminal imaging device, or an endoluminal data-acquisition device that is configured to acquire a plurality of functional endoluminal data points) may be determined. Based upon the determined locations within the blood vessel at which the endoluminal data points were acquired, the processor may generate an output, such as by generating an endoluminal imaging stack, and/or by generating an indication of the correspondence between an endoluminal data point and the location within the blood vessel at which the endoluminal data point was acquired.

For some applications, endoluminal data points are acquired by positioning an endoluminal data-acquisition device along a luminal segment of the blood vessel that includes a designated luminal site. Subsequently, while observing extraluminal images of the luminal segment, one or more locations along that segment are indicated by a user input device (e.g., user interface 30). In response to the indication of the one or more locations by the user input device, the corresponding, previously-acquired endoluminal images are displayed.

Typically, the designated luminal site includes a site being diagnosed, at which, subject to the outcome of the diagnosis, a therapeutic device will be positioned and deployed, e.g., the site of an anatomical feature, the implantation site of a previously-implanted device, and/or a site at a defined location with respect to the implantation site. For example, the designated luminal site may include a portion of the lumen that is narrow with respect to surrounding portions of the lumen, and/or the site of a lesion.

For some applications, endoluminal data points are acquired by positioning an endoluminal data-acquisition device at a designated luminal site. Subsequently, an endoluminal therapeutic device is positioned and deployed at the designated luminal site under extraluminal imaging, while concurrently viewing in real-time the endoluminal data that were previously acquired by the endoluminal data-acquisition device at the current location of the therapeutic device. Typically, endoluminal data are acquired at respective endoluminal sites in the vicinity of the designated endoluminal site. Subsequently, when the endoluminal therapeutic device is placed inside the lumen, previously-acquired endoluminal data are displayed and updated, typically automatically and typically in real-time, to correspond to the current location of the therapeutic device (or of a portion thereof), the location of the therapeutic device typically changing during the positioning of the therapeutic device.

For some applications, extraluminal imaging and the previously-acquired endoluminal data points are co-used such that it is as if the therapeutic device is being positioned and deployed under both real-time extraluminal imaging and real-time endoluminal data acquisition. This is because (a) the extraluminal imaging is performed in real-time, and (b), although the endoluminal data are not acquired in real-time, endoluminal data are displayed that correspond to the current location of the therapeutic device.

In accordance with some applications of the present invention, when the therapeutic device is disposed inside the lumen, the location of the device within the lumen is determined by performing image processing on the extraluminal image of the device inside the lumen.

For some applications, identification of the location of the tip of the radiopaque portion of the wire within a given image may be used to facilitate the determination of a transformation function for mapping between the image and a second image, for example, in accordance with techniques described in US 2014/0094691 to Steinberg and/or WO 13/175472 to Steinberg, both of which applications are incorporated herein by reference.

For example, a transformation function may be determined for mapping a current fluoroscopic image to a previously acquired angiographic image, or vice versa. For some applications, a transformation function is determined for mapping a current fluoroscopic image to a previously acquired angiographic image, by comparing an arrangement of two or more features within the current fluoroscopic image to a shape of at least a portion of a pathway within the previously acquired angiographic image. For some applications, at least one of the features is the radiopaque portion of the guidewire in the current fluoroscopic image.

For some applications, based upon the determined transformation function, the processor determines the location of an endoluminal device within the lumen, for example, in accordance with techniques described in US 2014/0094691 to Steinberg and/or WO 13/175472 to Steinberg, both of which applications are incorporated herein by reference. For example, the location within the blood vessel at which one or more endoluminal data points were acquired by the endoluminal data-acquisition device (e.g., an endoluminal imaging device, or an endoluminal data-acquisition device that is configured to acquire a plurality of functional endoluminal data points) may be determined. Based upon the determined locations within the blood vessel at which the endoluminal data points were acquired, the processor may generate an output, such as by generating an endoluminal imaging stack, and/or by generating an indication of the correspondence between an endoluminal data point and the location within the blood vessel at which the endoluminal data point was acquired. Alternatively, based upon the determined location within the blood vessel at which the endoluminal data point was acquired, the processor may co-use endoluminal data points and extraluminal imaging using techniques described hereinabove, and/or as described in US 2012/0004537 to Tolkowsky, US 2014/0094691 to Steinberg, and/or WO 13/175472 to Steinberg, which are incorporated herein by reference.

For some applications, identification of the location of the tip of the radiopaque portion of the wire within a given image may be used to facilitate the classification of a portion of the image as being associated with the distal end of a guidewire, for example, in accordance with techniques described in US 2014/0094691 to Steinberg, and/or WO 13/175472 to Steinberg, both of which applications are incorporated herein by reference. For example, classification of a portion of the image as being associated with the distal end of a guidewire may be used to facilitate the determination of a transformation function for mapping one image to another image, in accordance with techniques described in US 2014/0094691 to Steinberg, and/or WO 13/175472 to Steinberg, both of which applications are incorporated herein by reference.

Figure 6A:
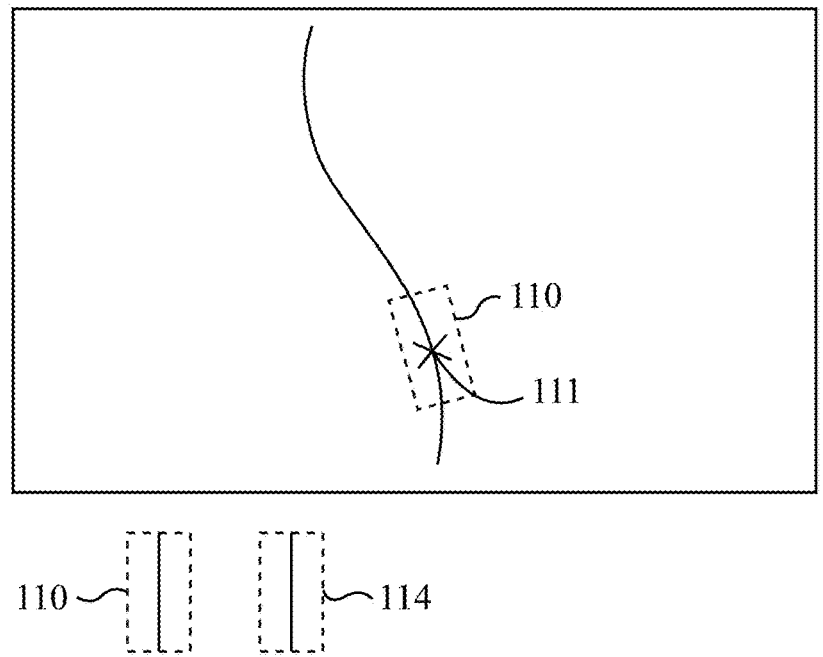
FIGS. 6A-B are schematic illustration of rectangular sampling regions of respective extraluminal images of a guidewire disposed inside a blood vessel, the regions being sampled using prior art techniques.
Figure 6B:
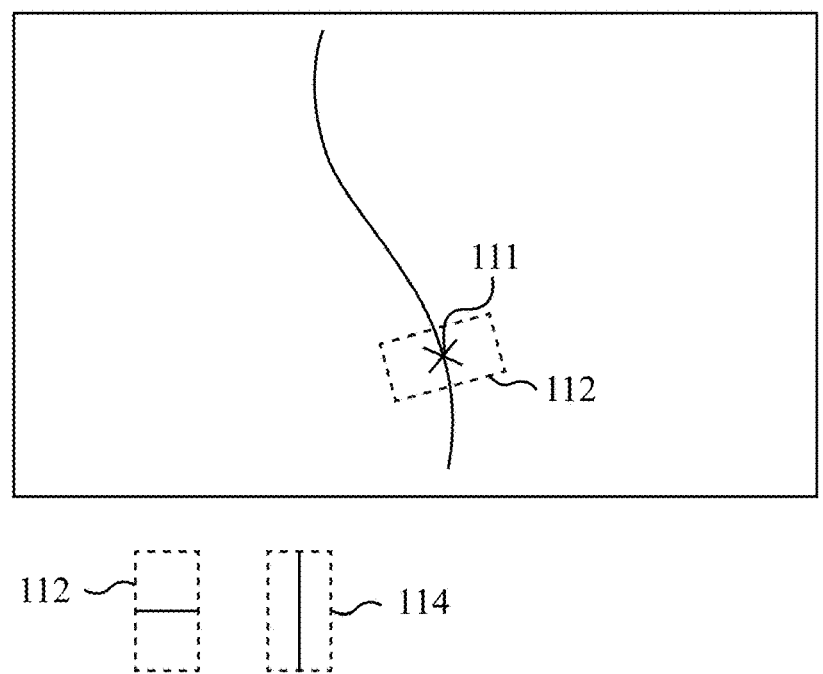

Reference is now made to FIGS. 6A-B, which are schematic illustration of rectangular sampling regions 110 and 112 of respective extraluminal images of a guidewire (such as guidewire 24) disposed inside a blood vessel, the regions being sampled using prior art techniques. Rectangular sampling region 110 of FIG. 6A is sampled such that the length of the rectangle is disposed approximately in parallel to the direction along which the guidewire is disposed locally within the image. A given pixel 111, which is at the center of the X in the image, is disposed at the center of the sampling region. Rectangular sampling region 112 of FIG. 6B is sampled such that the length of the rectangle is disposed approximately perpendicularly to the direction along which the guidewire is disposed locally within the image. Pixel 111, which is at the center of the X in the image, is disposed at the center of the sampling region.

The bottom of FIG. 6A shows sampling region 110 alongside a machine-learned appearance of a sampling region 114, a central pixel of which corresponds to a portion of a guidewire. The bottom of FIG. 6B shows sampling region 112 alongside sampling region 114. If machine-learning techniques are used by processor 28 to determine whether pixel 111 corresponds to a portion of the guidewire, by comparing sampling region 110 to region 114, then the processor is likely to determine that pixel 111 corresponds to a portion of the guidewire. However, if the processor compares sampling region 112 to region 114, then the processor is likely to determine that pixel 111 does not correspond to a portion of the guidewire.

In accordance with the description of FIGS. 6A-B, by sampling a rotationally-variant region around pixel 111, a machine-learning classifying algorithm may be unable to accurately determine whether pixel 111 corresponds to a portion of guidewire 24. In accordance with some applications of the present invention, in order to determine whether a given pixel corresponds to a portion of an object, a rotationally invariant region is sampled around the pixel, and machine learning classifying is applied to the rotationally invariant region, as described hereinbelow. For example, one or more of the following machine learning techniques may be used: Support Vector Machine (SVM), Deep Believe Networks, Neural Networks, and/or Random Decision Forest.

Figure 8A:
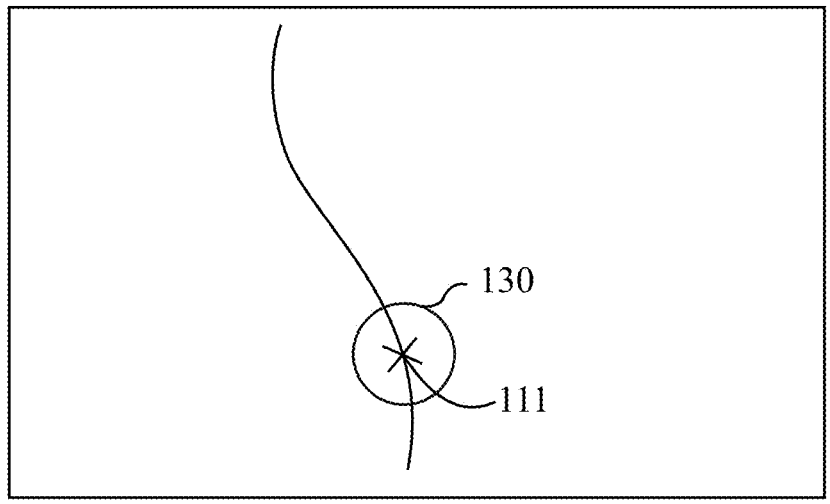
FIGS. 8A-B are schematic illustrations of an image of a guidewire, and a circular sampling region that is sampled around a pixel of the image, in accordance with some applications of the present invention.
Figure 8B:
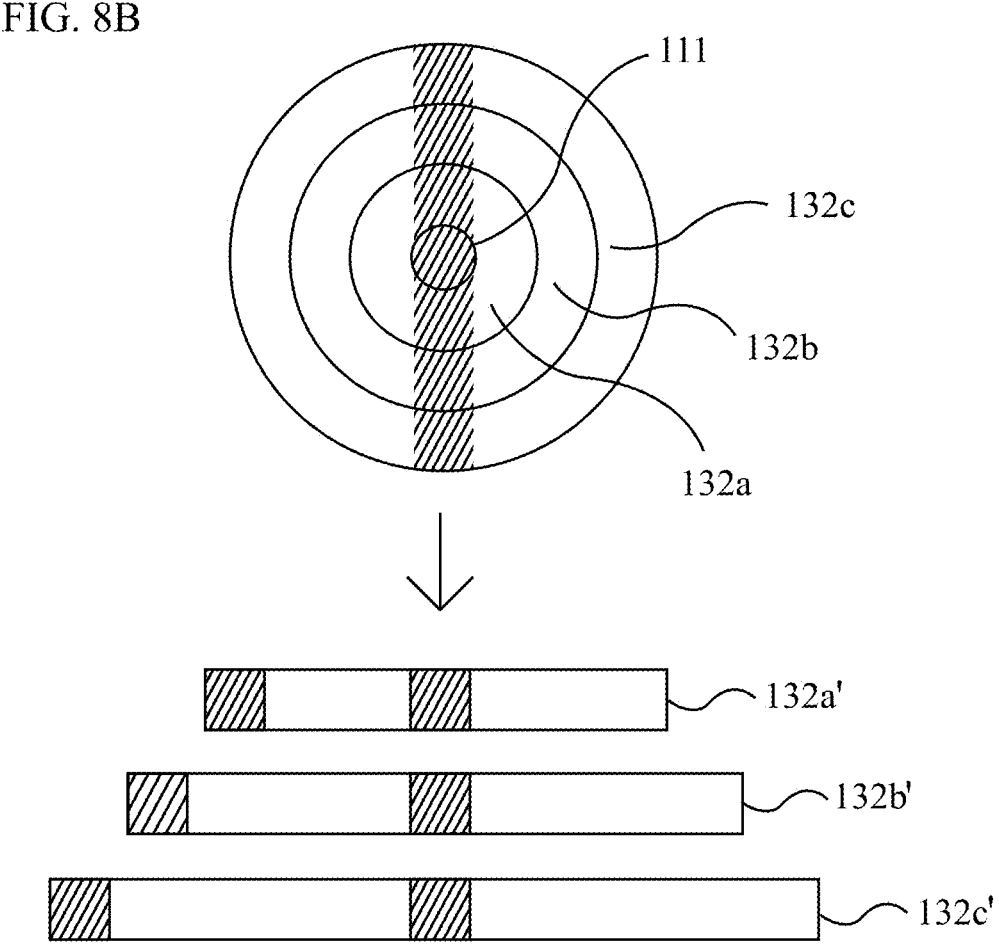

Reference is now made to FIG. 7, which is a flowchart showing steps of a procedure that is used to identify whether a given pixel within an image that contains an object corresponds to a portion of the object, in accordance with some applications of the present invention. Reference is also made to FIGS. 8A-B, which are schematic illustrations of an image of a guidewire, and a circular sampling region 130 that is sampled around pixel 111 of the image, the circular sampling region including a set of concentric circles 132a-132c that are disposed around pixel 111, in accordance with some applications of the present invention.

Typically, the procedure shown in FIG. 7 is performed with respect to an image (e.g., a fluoroscopic image) of a blood vessel of a subject, and is used to identify whether the given pixel within the image (e.g., pixel 111) corresponds to a portion of an object that is disposed inside the blood vessel. For example, the object disposed within the blood vessel may be a guide catheter 22, a wire (e.g., guidewire 24), a therapeutic endoluminal device, an endoluminal data-acquisition device, a radiopaque marker (such as marker 57, shown in FIG. 2B), and/or a stent.

As shown in FIG. 7, in a first step (step 120), processor 28 samples a set of concentric circles that are disposed around the pixel. For example, the top portion of FIG. 8B shows a set of concentric circles 132a-132c, which are sampled around pixel 111. The processor applies a first function to each of the circles, such that the circles are defined by a first set of rotationally invariant descriptors (step 122), typically, using one or more of the algorithms described herein. For example, the processor may apply a time-frequency domain transform (e.g., a Fourier transform, a discrete sine transform, and/or a discrete cosine transform) to the circles, and the processor may determine the absolute coefficients of the time-frequency domain transform of each of the circles. The effect of determining the absolute coefficients of the time-frequency domain transforms is to remove phase shifts from the transforms, such that the descriptors of two similar circles that have the same pattern but that are rotated with respect to one another are equal. Thus, at this stage, the circles are represented by respective rotationally invariant descriptors 132a'-132c', which are shown figuratively at the bottom of FIG. 8B.

Reference is now made to FIGS. 9A-B, which are schematic illustrations of regions of respective extra-luminal images, to which steps 120 and 122 of FIG. 7 are applied. FIG. 9A shows an image of a guidewire, with circular sampling region 130 sampled around pixel 111 of the image. FIG. 9B is an illustrative extraluminal image containing darkened pixels disposed around pixel 111, pixel 111 as shown in FIG. 9B not corresponding to a portion of a guidewire. In FIG. 9B, circular sampling region 130 is sampled around pixel 111 of the image.

The middle portions of FIGS. 9A and 9B show enlargements of circular sampling region 130, and the bottom portions of FIGS. 9A and 9B show sets of concentric circles 132a-132c that surround pixel 111. As described above, as a result of applying step 122 to concentric circles 132a-132c, the descriptors that represent circles 132a-132c become rotationally invariant. Therefore, since, apart from being rotated with respect to each other, the concentric circles shown in FIG. 9B are similar to those shown in FIG. 9A, the two sets of concentric circles will yield similar sets of rotationally invariant descriptors to one another, as a result of applying step 122 to the respective sets of circles. Therefore, in accordance with some applications of the present invention, steps 124, 126, and 127 of FIG. 7 are applied. The effect of applying steps 124, 126, and 127 is that concentric circles 132a-132c are represented by a descriptor that is rotationally invariant with respect to sampling region 130, and such that the rotational alignment of concentric circles 132a-132c with respect to each other is defined. Thus, after applying steps 124, 126, and 127, the representative descriptor of region 130 in FIG. 9A, is different from the representative descriptor of region 130 in FIG. 9B.

Referring again to FIG. 7, in step 124, processor 28 applies a second function to the set of circles 132a-132c such as to generate a second set of descriptors, each of the second set of descriptors representing a difference between respective pairs of the circles, typically, using one or more of the algorithms described herein. For example, the circles may be subtracted from another such that the second set of descriptors contains (a) a first descriptor that represents a difference between circles 132c and 132a, (b) a second descriptor that represents a difference between circles 132c and 132b, and (c) a third descriptor that represents a difference between circles 132b and 132a. In step 126, a third function is applied to the second set of descriptors, such that the second set of descriptors forms a second set of rotationally invariant descriptors, by becoming rotationally invariant, typically, using one or more of the algorithms described herein. For example, the processor may apply a time-frequency domain transform (e.g., a Fourier transform, a discrete sine transform, and/or a discrete cosine transform) to the second set of descriptors, and the processor may determine the absolute coefficients of the time-frequency domain transform of each of the second set of descriptors. For some applications, the second set of rotationally invariant descriptors is determined by calculating the differences between the rotationally invariant descriptors that are representative of the circles.

In step 127, which is optional (as indicated by the dashed box around step 127), the processor generates a representative descriptor that is representative of the first and second sets of rotationally invariant descriptors, typically using one or more of the algorithms described herein. Typically, the representative descriptor is generated by combining the first and second sets of rotationally invariant descriptors together, e.g., by listing the descriptors in combination with one another.

It is noted that steps 124 and 126 are typically performed in parallel with step 122 and are not necessarily performed subsequently and/or sequentially with respect to step 122. For some applications, step 124 (in which a second set of descriptors is generated that is representative of the differences between the circles) is performed prior to steps 122 and 126 (in which the first and second sets of rotationally invariant descriptors are generated) being performed. For some such applications, steps 122 and 126 are performed together with one another, for example, by applying a time-frequency domain transform (e.g., a Fourier transform, a discrete sine transform, and/or a discrete cosine transform) to both the set of circles and to the second set of descriptors that represents the differences between the circles, and then determining the absolute coefficients of the results of the time-frequency domain transform. As described hereinabove, for some applications, the second set of rotationally invariant descriptors is determined by calculating the differences between the rotationally invariant descriptors that are representative of the circles. Typically, the resultant set of absolute coefficients is a rotationally invariant descriptor that represents both the set of circles as well as the differences between the circles. Thus, for such applications, step 127 is performed automatically by virtue of performing steps 122 and 126.

As described hereinabove, the effect of applying steps 124, 126, and 127 of FIG. 7 is that concentric circles 132a-132c are represented by a descriptor that is rotationally invariant with respect to sampling region 130, but that describes the rotational alignment of concentric circles 132a-132c with respect to each other. Similarly, even if step 127 is not performed, the outputs of steps 122 and 126, when analyzed in combination with one another, represent concentric circles 132a-132c such that the circles are rotationally invariant with respect to sampling region 130, but such that the rotational alignment of concentric circles 132a-132c with respect to each other is defined.

In step 128, based upon the representative descriptor, the processor determines whether pixel 111 corresponds to a portion of the object (e.g., a portion of guidewire 24), typically using one or more of the algorithms described herein. Alternatively, for applications in which step 127 is not performed, the processor determines whether pixel 111 corresponds to a portion of the object, based upon the first and second sets of rotationally invariant descriptors. Typically, the processor determines whether pixel 111 corresponds to a portion of the object by applying machine-learning classifying to the representative descriptor that is yielded by step 127, and/or by applying machine-learning classifying to the first and second sets of rotationally invariant descriptors yielded by steps 122 and 126. In step 129, if the processor determines that pixel 111 corresponds to the portion of the object, the processor generates an output at least partially in response thereto.

It is noted that, for some applications, processor does not apply the procedure shown in FIG. 7 to all of the pixels in an image. For example, the processor may select pixels to which the procedure is applied by determining, for each pixel within at least a portion of the image, an objectness measure. The objectness measure typically measures an extent to which the pixel, together with other pixels within the image, forms a set of pixels having a given characteristic that is associated with the portion of the object. For example, if the object is a guidewire, the objectness measure may be similar to the wireness measure described hereinabove. For some applications, the objectness measure for other objects is generally similar to the wireness measure described hereinabove, mutatis mutandis. The processor may then select pixels to which to apply the procedure described shown in FIG. 7, by selecting pixels disposed in a vicinity of at least some pixels that form the set of pixels, and/or pixels that belong to the set of pixels.

As described hereinabove, typically, the procedure shown in FIG. 7 is performed with respect to an image (e.g., a fluoroscopic image) of a blood vessel of a subject, and is used to identify whether a given pixel within the image (e.g., pixel 111) corresponds to a portion of an object that is disposed inside the blood vessel. For example, the object disposed within the blood vessel may be a guide catheter 22, a wire (e.g., guidewire 24), a therapeutic endoluminal device, an endoluminal data-acquisition device, a radiopaque marker (such as marker 57, shown in FIG. 2B), and/or a stent. For some applications, the location of the object within the image is determined by performing the procedure shown in FIG. 7 with respect to a plurality of pixels within the image.

For some applications, in response to determining the location of the object within the image, the processor aligns the image with a second image, by aligning the object in each of the images with one another. In accordance with respective applications, the aligned images may be displayed in an image stream in which the images are aligned with one another, and/or a composite image may be generated based upon the alignment of the image and the second image. For example, the processor may average the image and the second image, subsequent to aligning the images with one another. In general, determining the location of the object within the image may be used to perform any of the image stabilization and/or enhancement techniques that are described in any one of US 2008/0221440 to Iddan, US 2012/0230565 to Steinberg, and US 2010/0222671 to Cohen, all of which applications are incorporated herein by reference.

For some applications, the location of the object within the image is used to facilitate the determination of the location of an endoluminal device within a lumen, for example, in accordance with techniques described in US 2012/0004537 to Tolkowsky, US 2014/0094691 to Steinberg, and/or WO 13/175472 to Steinberg, which are incorporated herein by reference. For example, the location within the blood vessel at which endoluminal data points were acquired by the endoluminal data-acquisition device (e.g., an endoluminal imaging device, or an endoluminal data-acquisition device that is configured to acquire functional endoluminal data points) may be determined. Based upon the determined location within the blood vessel at which the endoluminal data point was acquired, the processor may generate an output, such as by generating an endoluminal imaging stack, and/or by generating an indication of the correspondence between an endoluminal data point and the location within the lumen at which the endoluminal data point was acquired.

For some applications, the determined location of the object within the image is used to facilitate the determination of a transformation function for mapping between the image and a second image, for example, in accordance with techniques described in US 2014/0094691 to Steinberg, and/or WO 13/175472 to Steinberg, both of which applications are incorporated herein by reference. For example, a transformation function may be determined for mapping a current fluoroscopic image to a previously acquired angiographic image, or vice versa. For some applications, a transformation function is determined for mapping a current fluoroscopic image to a previously acquired angiographic image, by comparing an arrangement of two or more features within the current fluoroscopic image to a shape of at least a portion of a pathway within the previously acquired angiographic image. For some applications, at least one of the features is the object, the location of which is determined in the current fluoroscopic image using techniques described herein.

For some applications, based upon the determined transformation function, the processor determines the location of an endoluminal device within the lumen, for example, in accordance with techniques described in US 2014/0094691 to Steinberg, and/or WO 13/175472 to Steinberg, both of which applications are incorporated herein by reference. For example, the location within the blood vessel at which endoluminal data points were acquired by the endoluminal data-acquisition device (e.g., an endoluminal imaging device, or an endoluminal data-acquisition device that is configured to acquire functional endoluminal data points) may be determined. Based upon the determined location within the blood vessel at which the endoluminal data points were acquired, the processor may generate an output, such as by generating an endoluminal imaging stack, and/or by generating an indication of the correspondence between an endoluminal data point and the location within the lumen at which the endoluminal data point was acquired. Alternatively, based upon the determined location within the blood vessel at which the endoluminal data points were acquired, the processor may co-use endoluminal data points and extraluminal imaging using techniques described hereinabove, and/or as described in US 2012/0004537 to Tolkowsky, US 2014/0094691 to Steinberg, and/or WO 13/175472 to Steinberg, which are incorporated herein by reference.

For some applications, the determined location of the object within the image is used to facilitate the classification of a portion of the image as being associated with the object, for example, in accordance with techniques described in US 2014/0094691 to Steinberg, and/or WO 13/175472 to Steinberg, both of which applications are incorporated herein by reference. For example, classification of a portion of the image as being associated with the object may be used to facilitate the determination of a transformation function for mapping one image to another image, in accordance with techniques described in US 2014/0094691 to Steinberg, and/or WO 13/175472 to Steinberg, both of which applications are incorporated herein by reference.

Figure 11B:
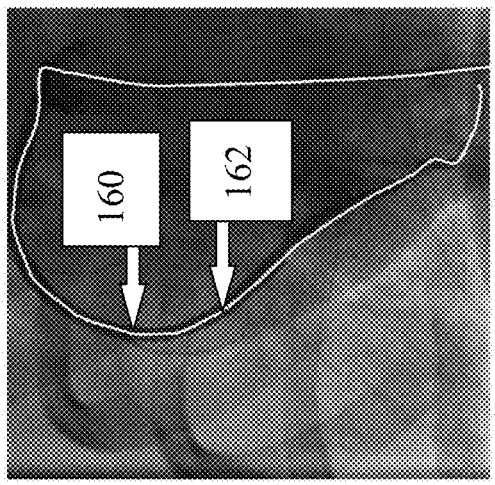
FIGS. 11A-C are schematic illustrations of images of a lumen (e.g., an artery) of a subject, in accordance with some applications of the present invention.
Figure 11A:
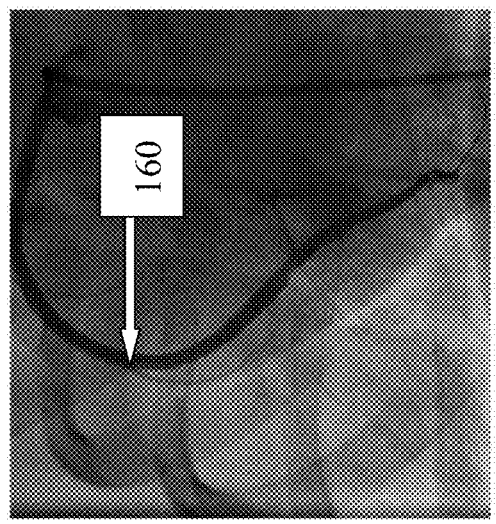
Figure 11C:

Reference is now made to FIG. 10, which is a flowchart showing steps of a procedure that is used to determine a transformation function for mapping between a location within a roadmap image of a lumen and a location within a second image of the lumen, in accordance with some applications of the present invention. Reference is also made to FIGS. 11A-C, which are schematic illustrations of images of a lumen (e.g., an artery) 160 of a subject, in accordance with some applications of the present invention.

In a first step 140 of the procedure, at least one first extraluminal image of the lumen is acquired. Typically, a first set of extraluminal images of the lumen are acquired using an extraluminal imaging device. For example, extraluminal imaging device 20 (FIG. 1) may be used to acquire a first set of extraluminal images of a blood vessel (e.g., a coronary artery) of the subject. In accordance with respective applications, the first set of extraluminal images is acquired in a presence of contrast agent within the lumen, or in an absence of contrast agent within the lumen.

In step 142, processor 28 designates the at least one first extraluminal image as a roadmap image. Typically, a first set of extraluminal images is acquired, and the processor designates at least one of the first set of images as the roadmap image, using one or more of the algorithms described herein. Typically, at least one of the first set of images is designated as the roadmap image in accordance with techniques described in US 2014/0094691 to Steinberg, and/or WO 13/175472 to Steinberg, both of which applications are incorporated herein by reference. For example, the image may be selected based upon the following criteria: (a) the image is acquired at a desired cardiac phase (typically end diastole) and/or (b) in the image, contrast agent highlights the lumen. For procedures in which the techniques described herein are performed on a subject's coronary arteries, an image may be selected from the set of images based upon visibility of at least a portion of the coronary arteries in the set of images. For some applications, an angiogram with the greatest visibility of coronary arteries is selected, with such selection typically being automatic. The greatest visibility is typically determined based upon the greatest total number of arteries observed, the greatest number of image pixels attributed to an artery, and/or the greatest image contrast in the appearance of specific arteries. For some applications, an extraluminal image that is based upon a plurality of extraluminal images (e.g., an image that is based upon averaging a plurality of images) is selected and designated as the roadmap image.

FIG. 11A shows an image of a subject's arteries that has been designated as a roadmap image, in accordance with some applications of the present invention. It may be observed that, in the roadmap image, an artery 160 is highlighted with contrast agent.

Referring again to FIG. 10, in step 144, processor 28 designates a roadmap pathway within the roadmap image, typically using one or more of the algorithms described herein. Typically, the roadmap pathway is designated in accordance with the techniques described in US 2014/0094691 to Steinberg and/or WO 13/175472 to Steinberg, both of which applications are incorporated herein by reference. For some applications, the roadmap pathway is designated in response to a manual user input, and/or automatically. For example, the pathway may be designated by the user indicating some points along the path and the processor completing the path, based upon the manually-indicated points. For some applications, the roadmap pathway is at least partially determined by determining the centerlines of the lumen. For example, the centerlines of the lumen may be determined using techniques for determining the centerline of a lumen described in US 2012/0230565, WO 10/058398, WO 12/014212, and/or US 2012/0004537, all of which applications are incorporated herein by reference.

For some applications, the first extraluminal image (or the first set of extraluminal images) is acquired in the absence of contrast agent within the lumen. For such applications, the roadmap pathway may be designated by identifying a set of features within the roadmap image, and designating the roadmap pathway in response to the identified set of features. Typically the set of features correspond to radiopaque features (such as radiopaque markers, and/or a radiopaque tip of a guide catheter) that are disposed inside the lumen. Thus, the set of features are typically indicative of a location of the lumen within the image.

FIG. 11B shows the roadmap image of FIG. 11A, with a roadmap pathway 162 having been designated within artery 160. It is noted that, although, in FIG. 11B, pathway 162 is displayed within the roadmap image, for some applications, the roadmap pathway is designated without the path actually being displayed on a display.

Referring again to FIG. 10, in step 146, an extraluminal imaging device (e.g., extraluminal imaging device 20, shown in FIG. 1) acquires an additional extraluminal image, and, typically, acquires a second set of extraluminal images. Typically, the second set of extraluminal images are fluoroscopic images, at least some of which are acquired in an absence of contrast agent within the lumen, and, further typically, while an endoluminal device (e.g., an endoluminal data-acquisition device, or an endoluminal therapeutic device) is disposed within the lumen.

FIG. 11C shows an example of an extraluminal image acquired in an absence of contrast agent within the lumen. It may be observed that, in FIG. 11C, the lumen itself is not highlighted with contrast agent, although there are darkened portions of the image corresponding to radiopaque objects that are disposed within the lumen.

In step 148, based upon the additional extraluminal image (e.g., based upon at least one image belonging to a second set of extraluminal images), processor 28 generates a score image, by applying a scoring function to at least some pixels within the image, such that each of the pixels to which the scoring function is applied is designated a score that is indicative of an extent to which the pixel has a given characteristic.

Typically, the score image is generated using one or more of the algorithms described herein. It is noted that, for some applications, the scoring function does not result in identifying a pixel as corresponding to a given object (such as a guide catheter, a wire, or a radiopaque marker). Alternatively, the scoring function may result in identifying one or more pixels as corresponding to a given object (such as a guide catheter, a wire, or a radiopaque marker). For some applications, in step 148, a single filter is applied to the image. For example, a Hessian filter or a high pass filter may be applied to at least a portion of the image. For some applications, the scoring function designates a score to each of the pixels that is indicative of an intensity of the pixel. Alternatively or additionally, the scoring function designates a score to each of the pixels that is indicative of an extent to which the pixel is likely to correspond to a non-anatomical object.

In step 150, based upon the scores of at least some of the pixels to which the scoring function was applied, processor 28 determines a correspondence between at least a portion of the roadmap pathway and a curve within the score image. Typically, the correspondence between at least a portion of the roadmap pathway and a curve within the score image is determined using one or more of the algorithms described herein. Typically, the processor determines the correspondence between the portion of the roadmap pathway and the curve within the score image, by applying a best-fit algorithm, such as to best fit the roadmap pathway to pixels of the image, the scores of which pixels indicate that the pixels are likely to correspond to pixels of the roadmap pathway. For example, the processor may determine that pixels that are darker than other pixels are likely to correspond to pixels along the roadmap pathway. Alternatively or additionally, the processor may determine that pixels that have a score that is indicative of the pixels corresponding to a non-anatomical object are likely to correspond to pixels along the roadmap pathway.

For some applications, processor 28 uses a dynamic-programming algorithm to determine the correspondence between a portion of the roadmap pathway and a curve within the score image. For example, the processor may determine a correspondence between a first pixel along the roadmap pathway and a first pixel of the additional extraluminal image. Subsequently, the processor may determine a correspondence between a second pixel along the roadmap pathway and a second pixel of the additional extraluminal image, based upon (a) the determined correspondence between the first pixel along the roadmap pathway and the first pixel of the additional extraluminal image, and (b) the scores of at least some of the pixels to which the scoring function was applied.

Alternatively or additionally, processor 28 uses a gradient-descent algorithm to determine the correspondence between a portion of the roadmap pathway and a curve within the score image. For some applications, the processor uses a gradient-descent algorithm that includes a regularization function. The effect of the regularization function is that pixels that are disposed in a given sequence in the additional extraluminal image are determined to correspond to respective pixels along the roadmap pathway, the corresponding pixels being disposed along the roadmap pathway in the same given sequence.

Referring again to FIG. 10, in step 152, based upon the correspondence between the portion of the roadmap pathway and the curve within the score image, processor 28 determines a transformation function for mapping between a location within the roadmap image and a location within the additional extraluminal image. Typically, between the acquisition of the roadmap image, and the acquisition of the additional extraluminal image, the lumen has undergone changes in location and shape (e.g., due to the subject's respiratory cycle, due to the subject's cardiac cycle, due to other movement of the subject, and/or due to the devices within the lumen having moved the lumen). Typically, in step 152, the processor determines an estimated measure of a transformation (e.g., stretching, rotation, shrinking, perspective, skew, etc.) that should be applied to the additional extraluminal image, such that locations within the additional extraluminal image may be mapped to corresponding locations within the roadmap image, and/or vice versa. For some applications, techniques described herein are combined with algorithms for mapping an extraluminal image to a roadmap image as described in US 2014/0094691 to Steinberg, and/or WO 13/175472 to Steinberg, both of which applications are incorporated herein by reference.

For example, in order to perform the mapping, the mapping functionality may assume that the general shape of the lumen, and the relationships among features along the lumen, are generally preserved throughout the motion of the lumen. In order to find the desired index mapping, a deformation measure is defined for each possible mapping, and the desired mapping is obtained by minimizing the deformation measure, as described in US 2014/0094691 to Steinberg, and/or WO 13/175472 to Steinberg, both of which applications are incorporated herein by reference.

Referring again to FIG. 10, in step 154 processor 28 generates an output on output device 40, in response to the determined transformation function.

For some applications, processor 28 calibrates the roadmap pathway by determining the relationship between the physical dimension of a portion of the lumen and a number of pixels in a portion of the roadmap pathway that corresponds to the portion of the lumen (e.g., the length in mm along the lumen, per pixel along the roadmap pathway). It is noted that typically, the calibration factors associated with respective portions of a lumen in an image varies, due to respective portions of the lumen being disposed at respective angles with respect to the extraluminal imaging device. Therefore, typically, the processor determines a plurality of local calibration factors along the roadmap pathway. For some applications, in response to the determined transformation function, processor determines localized calibration factors along the roadmap pathway, using generally similar techniques to those described in US 2014/0094691 to Steinberg, and/or WO 13/175472 to Steinberg, both of which applications are incorporated herein by reference.

For some applications, based upon the determined transformation function, the processor determines the location of an endoluminal device within the lumen, for example, in accordance with techniques described in US 2014/0094691 to Steinberg, and/or WO 13/175472 to Steinberg, both of which applications are incorporated herein by reference. For example, the additional extraluminal image may be acquired while the endoluminal device is inside the lumen. Based upon the transformation function, the processor may determine the location of the endoluminal device with respect to the roadmap image, and may generate an output indicative of the determined location of the endoluminal device with respect to the roadmap image. For some applications, the output indicative of the determined location of the endoluminal device with respect to the roadmap image is generated by the processor in real-time, and/or on-line with respect to acquisition of the image belonging to the second set of images.

For some applications, respective transformation functions are determined for mapping between locations within the roadmap image and locations within respective images belonging to the second set of extraluminal images. Based upon the mapping, locations of the endoluminal device in respective extraluminal images of the second set of extraluminal images are determined, with respect to the roadmap image.

For some applications, the endoluminal device is an endoluminal data-acquisition device (e.g., an endoluminal imaging device, or an endoluminal data-acquisition device that is configured to acquire a plurality of functional endoluminal data points). Based upon the locations of the endoluminal device in the respective extraluminal images with respect to the roadmap image, the processor determines the location within the lumen at which one or more endoluminal data points were acquired by the endoluminal data-acquisition device.

For example, based upon the determined locations within the lumen at which the endoluminal data points were acquired, the processor may generate an output, such as by generating an endoluminal imaging stack, and/or by generating an indication of the correspondence between an endoluminal data point and the location within the lumen at which the endoluminal data point was acquired. Alternatively, based upon the determined locations within the lumen at which the endoluminal data point was acquired, the processor may co-use endoluminal data points and extraluminal imaging using techniques described hereinabove, and/or as described in US 2012/0004537 to Tolkowsky, US 2014/0094691 to Steinberg, and/or WO 13/175472 to Steinberg, which are incorporated herein by reference.

For some applications, by performing the mapping on images belonging to the second set of extraluminal images, for each of the extraluminal images to which the mapping is applied, an estimate is determined of where, at the time when an extraluminal data point (e.g., image) was acquired, the endoluminal data-acquisition device was disposed with respect to the roadmap pathway. In particular, for each of the extraluminal images to which the mapping is applied, an estimate is determined of where, at the time when the extraluminal image was acquired, the data-acquiring portion of the data-acquisition device (e.g., the endoluminal data-acquisition device head) was disposed upon the roadmap pathway.

Typically, processor 28 determines which endoluminal data points were acquired at the same time as respective extraluminal images. For example, a single computer (or two or more computers that are time-synchronized) may operate both the extraluminal imaging and the endoluminal data-acquisition, and the computer may log the times at which extraluminal images and endoluminal data-points were acquired. Or, the processor may determine which endoluminal data points were acquired at the same time as respective extraluminal images based upon known frame rates at which the extraluminal images and the endoluminal data points are acquired. By determining an estimate of where, at the time when the extraluminal image was acquired, the data-acquiring portion of the data-acquisition device (e.g., the endoluminal data-acquisition device head) was disposed with respect to the roadmap image, the processor determines the location of the endoluminal data point that was acquired at the same time as the extraluminal image, with respect to the roadmap image.

For some applications, processor 28 performs interpolation on the determined locations of the data-acquiring portion of the endoluminal data-acquisition device with respect to the roadmap image, such as to determine the location of the data-acquiring portion of the endoluminal data-acquisition device with respect to the roadmap image at any time during the movement of the endoluminal data-acquisition device with respect to the lumen (i.e., even at times between acquisitions of extraluminal images belonging to the second set of extraluminal images). For some applications, generally similar techniques to those described in US 2014/0094691 to Steinberg, and/or WO 13/175472 to Steinberg, both of which applications are incorporated herein by reference, are used for performing the interpolation.

Typically, the interpolation is performed by optimizing a cost of a trajectory of the endoluminal data-acquisition device, throughout the movement of the endoluminal data-acquisition device with respect to the lumen. The cost includes parameters such as maintaining a given separation between given features (e.g., between pairs of markers), the velocity of the endoluminal data-acquisition device, movement continuity, and quality of the mapping of the guide catheter. The resulting trajectory is smoothed and the result is a floating point model index of endoluminal data-acquisition device locations along the roadmap image. For some applications, the interpolation is performed by applying parameter estimation techniques to the determined locations of the data-acquiring portion of the endoluminal data-acquisition device along the roadmap image. For example, temporal filtration techniques, and/or outlier removal techniques may be applied to the determined locations of the data-acquiring portion of the endoluminal data-acquisition device along the roadmap pathway.

For some applications, in order to perform the interpolation, at least a portion of the roadmap image (e.g., the roadmap pathway) is first calibrated, e.g., using techniques described hereinabove, and/or in US 2014/0094691 to Steinberg and/or WO 13/175472 to Steinberg, both of which applications are incorporated herein by reference.

As described hereinabove, typically, a portion of the endoluminal data points are acquired at the same time as respective extraluminal images. For these endoluminal data points, processor 28 determines the locations of the endoluminal data points with respect to the roadmap image by mapping between extraluminal images corresponding to respective endoluminal data points, and the roadmap image, as described hereinabove. Further typically, a second portion of the endoluminal data points are acquired between acquisitions of extraluminal images of the lumen. For these endoluminal data points, processor 28 typically determines the locations of the endoluminal data points with respect to the roadmap image, using interpolation techniques.

For some applications, processor 28 only shows the correspondence between the first portion of the endoluminal data points and locations within the roadmap image. For example, in response to an input from a user (e.g., via user interface 30), the processor may only show the correspondence between the first portion of the endoluminal data points and locations within the roadmap image. Alternatively or additionally, the processor may generate a stack of endoluminal data points (e.g., an endoluminal image stack) using only endoluminal images belonging to the first portion of endoluminal images.

For some applications, the processor shows the correspondence between both the first and second portions of endoluminal data points and locations within the roadmap image, and/or generates a stack of endoluminal data points using endoluminal images belonging to both of the first and second portions of endoluminal data points). In addition, the processor generates an indication of which of the endoluminal data points belong to the first portion of endoluminal data points, and which of the endoluminal data points belong to the second portion of endoluminal data points, e.g., using a color scheme, or an alternative graphical feature to differentiate between endoluminal data points belonging to the first and second portions of endoluminal data points.

For some applications, the above-described techniques for distinguishing between the first and second portions of endoluminal data points are performed in combination with mapping techniques for mapping between extraluminal images and a roadmap image, as described in US 2014/0094691 to Steinberg, and/or WO 13/175472 to Steinberg, both of which applications are incorporated herein by reference.

It is noted that although some techniques described herein are described primarily with respect to extraluminal fluoroscopic/angiographic images and endoluminal images, the scope of the present invention includes applying the techniques described herein to other forms of extraluminal and endoluminal images and/or data, mutatis mutandis. For example, the extraluminal images may include images generated by fluoroscopy, CT, MRI, ultrasound, PET, SPECT, other extraluminal imaging techniques, or any combination thereof. Endoluminal images may include images generated by intravascular ultrasound (IVUS) optical coherence tomography (OCT), near-infrared spectroscopy (NIRS), intravascular ultrasound (IVUS), endobronchial ultrasound (EBUS), magnetic resonance (MR), other endoluminal imaging techniques, or any combination thereof. Endoluminal data may include data related to pressure (e.g., fractional flow reserve), flow, temperature, electrical activity, or any combination thereof.

Although some techniques described herein are described primarily as being performed on a blood vessel, the scope of the present application includes performing similar techniques on a lumen in the vascular system, the respiratory tract, the digestive tract, the urinary tract, any other luminal structure within a patient's body, or any other suitable anatomical structure within a patient's body, mutatis mutandis. Examples of an anatomical structure to which the techniques described herein may be applied include a coronary vessel, a coronary lesion, a vessel, a vascular lesion, a lumen, a luminal lesion, and/or a valve.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that each block of the flowcharts shown in FIGS. 3A-C, 5, 7 and 10 and combinations of blocks in the flowchart, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIGS. 2A-C and 3A-C, computer processor 28 typically acts as a special purpose device-specific parameter measurement computer processor. When programmed to perform the algorithms described with reference to FIGS. 4 and 5, computer processor 28 typically acts as a special purpose guidewire-tip-identifying computer processor. When programmed to perform the algorithms described with reference to FIG. 7, computer processor 28 typically acts as a special purpose object-identifying computer processor. When programmed to perform the algorithms described with reference to FIG. 10, computer processor 28 typically acts as a special purpose image-mapping computer processor. Typically, the operations described herein that are performed by computer processor 28 transform the physical state of memory 29, which is a real physical article, to have a different magnetic polarity, electrical charge, or the like depending on the technology of the memory that is used.

The scope of the present application includes combining the apparatus and methods described herein with apparatus and methods described in any one of the following applications, all of which are incorporated herein by reference:

International Application PCT/IL2008/000316 to Iddan (published as WO 08/107905), filed Mar. 9, 2008, entitled "Imaging and tools for use with moving organs."

U.S. patent application Ser. No. 12/075,252 to Iddan (published as US 2008/0221440), filed Mar. 10, 2008, entitled "Imaging and tools for use with moving organs;"

International Application PCT/IL2009/000610 to Iddan (published as WO 09/153794), filed Jun. 18, 2009, entitled "Stepwise advancement of a medical tool;"

U.S. patent application Ser. No. 12/487,315 to Iddan (published as US 2009/0306547), filed Jun. 18, 2009, entitled "Stepwise advancement of a medical tool;"

U.S. patent application Ser. No. 12/666,879 to Steinberg (published as US 2012/0230565), which is the US national phase of PCT Application No. PCT/IL2009/001089 to Cohen (published as WO 10/058398), filed Nov. 18, 2009, entitled "Image processing and tool actuation for medical procedures;"

U.S. patent application Ser. No. 12/781,366 to Cohen (published as US 2010/0222671), filed May 17, 2010, entitled "Identification and presentation of device-to-vessel relative motion;"

International Patent Application PCT/IL2011/000391 to Cohen (published as WO 11/145094), filed May 17, 2011, entitled "Identification and presentation of device-to-vessel relative motion;"

U.S. Ser. No. 13/228,229 to Tolkowsky (published as US 2012/0004537), filed Sep. 8, 2011, which is a continuation of International Application No. PCT/IL2011/000612 to Tolkowsky (published as WO 12/014212), filed 28 July, 2011 entitled "Co-use of endoluminal data and extraluminal imaging;"

U.S. patent application Ser. No. 14/128,243 to Barzelay (published as US 2014/0140597), which is the US national phase of International Patent Application PCT/IL2012/000246 (published as WO 12/176191), filed Jun. 21, 2012, entitled "Luminal background cleaning;"

U.S. patent application Ser. No. 13/228,229 to Tolkowsky (published as US 2012/0004537), filed Sep. 8, 2011, entitled "Co-use of endoluminal data and extraluminal imaging;"

U.S. patent application Ser. No. 14/097,922 to Steinberg (published as US 2014/0094691), filed Dec. 5, 2013, entitled "Co-use of endoluminal data and extraluminal imaging," which is a continuation of International Application PCT/IL2013/050438 (published as WO 13/175472) to Steinberg, filed May 21, 2013, entitled "Co-use of endoluminal data and extraluminal imaging;"

U.S. patent application Ser. No. 14/142,082 to Tolkowsky (published as US 2014/0121513), filed Dec. 27, 2013, entitled "Determining a characteristic of a lumen by measuring velocity of a contrast agent," which is a continuation of International Application PCT/IL2013/050549 (published as WO 14/002095) to Tolkowsky, filed Jun. 26, 2013, entitled "Flow-related image processing in luminal organs;" and International Patent Application PCT/IL2015/050372 to Klaiman, filed Apr. 2, 2015, entitled "Image analysis in the presence of a medical device," which claims priority from U.S. Provisional Patent Application 61/977,891 to Klaiman, filed Apr. 10, 2014, entitled "Image analysis in the presence of a medical device."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
   a display; and
   a computer processor in communication with the display and an extraluminal imaging device, wherein the computer processor is configured to:
   receive, from the extraluminal imaging device, an extraluminal image of:
      a lumen within a subject; and
      an endoluminal device positioned within the lumen; and
   determine whether a given pixel of the extraluminal image corresponds to the endoluminal device based on:
      a first set of descriptors defining a plurality of concentric circles around the given pixel; and
      a second set of descriptors, wherein each of the second set of descriptors represents a difference between respective pairs of the plurality of concentric circles; and
   generate an output for display on the display in response to determining that the given pixel corresponds to the endoluminal device.

2. The apparatus of claim 1, wherein the computer processor determining whether the given pixel of the extraluminal image corresponds to the endoluminal device comprises:
   applying machine-learning classifying to the first and second sets of descriptors.

3. The apparatus of claim 1, wherein the computer processor is configured to:
   select the given pixel, wherein selecting the given pixel comprises:
      for each pixel within the extraluminal image, determining an objectness measure that measures an extent to which the pixel, together with other pixels within the extraluminal image, forms part of a set of pixels having a given characteristic that is associated with the endoluminal device; and
   selecting at least one of:
      a pixel disposed in a vicinity of some pixels that form part of the set of pixels, or
      a pixel that belongs to the set of pixels.

4. The apparatus of claim 1,
   wherein the lumen comprises a blood vessel of the subject, and
   wherein the endoluminal device is positioned within the blood vessel.

5. The apparatus of claim 1, wherein the endoluminal device comprises at least one of a catheter, a guidewire, an endoluminal therapeutic device, or an endoluminal data-acquisition device.

6. The apparatus of claim 1, wherein the computer processor is configured to:
   align the extraluminal image with a second extraluminal image, in response to identifying that the given pixel corresponds to the endoluminal device.

7. The apparatus of claim 6, wherein the output comprises the extraluminal image and the second extraluminal image in an image stream in which the extraluminal image and the second extraluminal image are aligned with one another.

8. The apparatus of claim 6, wherein the output comprises a composite image based on alignment of the extraluminal image and the second extraluminal image.

9. The apparatus of claim 1,
   wherein the computer processor is configured to determine a transformation function for mapping between the extraluminal image and a second extraluminal image, in response to identifying that the given pixel corresponds to the endoluminal device, and
   wherein the computer processor is configured to generate the output based on the transformation function.

10. The apparatus of claim 9,
    wherein the lumen comprises a blood vessel of the subject, wherein the endoluminal device is positioned within the blood vessel, wherein the computer processor is configured to determine a location of the endoluminal device within the blood vessel, based on the transformation function, and wherein the computer processor is configured to generate the output based on the location of the endoluminal device within the blood vessel.

11. The apparatus of claim 10, wherein the endoluminal device comprises an endoluminal data-acquisition device, wherein the computer processor is configured to determine a location within the blood vessel at which an endoluminal data point was acquired by the endoluminal data-acquisition device, based the location of the endoluminal device within the blood vessel, and wherein the computer processor is configured to generate the output based on the location within the blood vessel at which the endoluminal data point was acquired by the endoluminal data-acquisition device.

* * * * *